(12) United States Patent
Fischer et al.

(10) Patent No.: US 7,332,512 B2
(45) Date of Patent: Feb. 19, 2008

(54) HALOGENATED NITROBUTADIENES FOR CONTROLLING ANIMAL PESTS

(75) Inventors: Reiner Fischer, Monheim (DE); Peter Jeschke, Bergisch Gladbach (DE); Christoph Erdelen, deceased, late of Leichlingen (DE); by Angelika Lubos-Erdelen, legal representative, Leichlingen (DE); Peter Lösel, Leverkusen (DE); Udo Reckmann, Köln (DE); Dieter Kaufmann, Goslar (DE); Viktor Zapolskil, Clausthal-Zellerfeld (DE)

(73) Assignee: Bayer CropScience AG, Monheim (DE)

( * ) Notice: Subject to any disclaimer, the term of this patent is extended or adjusted under 35 U.S.C. 154(b) by 575 days.

(21) Appl. No.: 10/494,212

(22) PCT Filed: Oct. 23, 2002

(86) PCT No.: PCT/EP02/11844

§ 371 (c)(1),
(2), (4) Date: Nov. 12, 2004

(87) PCT Pub. No.: WO03/040129

PCT Pub. Date: May 15, 2003

(65) Prior Publication Data

US 2005/0080272 A1   Apr. 14, 2005

(30) Foreign Application Priority Data

Nov. 5, 2001  (DE) ............................... 101 54 313

(51) Int. Cl.
*A61K 31/44* (2006.01)
*C07D 207/46* (2006.01)
*C07C 211/42* (2006.01)

(52) U.S. Cl. ................. 514/357; 546/249; 548/571; 564/336

(58) Field of Classification Search ............... 546/249, 546/184; 564/336
See application file for complete search history.

(56) References Cited

U.S. PATENT DOCUMENTS

| | | | |
|---|---|---|---|
| 4,678,795 A | 7/1987 | Shiokawa et al. | 514/341 |
| 4,742,060 A | 5/1988 | Shiokawa et al. | 514/252 |
| 4,774,247 A | 9/1988 | Shiokawa et al. | 514/256 |
| 4,812,571 A | 3/1989 | Shiokawa et al. | 546/296 |
| 4,845,106 A | 7/1989 | Shiokawa et al. | 514/342 |
| 4,968,695 A | 11/1990 | Wolf et al. | 514/63 |
| 5,001,138 A | 3/1991 | Shiokawa et al. | 514/342 |
| 5,164,508 A | 11/1992 | Diehr | 546/329 |
| 5,204,360 A | 4/1993 | Shiokawa et al. | 514/342 |
| 5,298,507 A | 3/1994 | Shiokawa et al. | 514/256 |
| 5,352,794 A | 10/1994 | Lantzsch | 546/329 |
| 5,424,437 A | 6/1995 | Ieno et al. | 546/329 |
| 5,428,032 A | 6/1995 | Shiokawa et al. | 514/226.8 |
| 5,461,167 A | 10/1995 | Shiokawa et al. | 548/202 |
| 5,580,889 A | 12/1996 | Shiokawa et al. | 514/343 |
| 5,750,704 A | 5/1998 | Shiokawa et al. | 546/275.1 |
| 6,022,967 A | 2/2000 | Shiokawa et al. | 544/298 |
| 6,297,374 B1 | 10/2001 | Shiokawa et al. | 544/55 |

FOREIGN PATENT DOCUMENTS

| | | |
|---|---|---|
| JP | 4-217975 | 8/1992 |
| JP | 5-70431 | 3/1993 |
| JP | 5-310697 | 11/1993 |
| JP | 6-16636 | 1/1994 |
| JP | 7-242633 | 9/1995 |
| WO | 94/29268 | 12/1994 |
| WO | 97/24032 | 7/1997 |

OTHER PUBLICATIONS

Translation for Zhurnal Organicheskoi Khimii, vol. 15, No. 6, pp. 1321-1322, Jun. 1979, Yu. A. Ol'dekop et al, " 4-Bromo- 1,1,3,4-Tetrachloro-2-Nitro-1,3-Butadiene", Institue of Physical Organic Chemistry, Academy of Sciences of Belorussian SSR., pp. 1180-1181.
Translation for Zhurnal Organicheskoi Khimii, vol. 12, No. 9, pp. 2039-2040, Sep. 1976, Yu A. Ol'dekop et al, "2-Nitropentachloro-1,3-Butadiene", Institute of Physical Organic Chemistry, Academy of Sciences of Belorussian SSR., p. 1986.
Dokl. Nats. Akad. Nauk. Belarusi, 40, 1, (month unavailable) 1996, V.I. Potkin et al, pp. 68-71, "Nitration of 2-H-pentachloro-1, 3-Butadiene".
Dokl. Nats. Akad. Naul. Belarusi, 42, 2, (month unavailable) 1998, pp. 75-78, N.I. Nechai et al, "Synthesis and Certain Characteristics of 1,3-Dinitro-1,2,4,4-Tetrachloro-1,3-Butadiene".
Russ. J. Org. Chem., 35, 3, (month unavailable) 1999, pp. 445-450, V.A. Zapol'ski et al, "Azolyl Derivatives of Halonitrobutadienes: III. Reaction of 2-(2,3,3-Trichloro-1-nitro-2-propenylidene)azoles with Amines".
Russ. J. Org. Chem., 33, 11, (month unavailable) 1997, pp. 1632-1637, V.A. Zapol'skii et al, "Azolyl Derivatives of Halonitrobutadienes. II. Synthesis and Some Reactions of 1,1-Bis(3,5-dimethylpyrazol-1-yl)- and 1,1-Bis(1,2,4-triazol-1-yl)-2-nitrotrihalo-1,3-butadienes".
Biosci. Biotechnol. Biochem. 62(6), (month unavailable) 1998, pp. 1216-1224, Shinzo Kagabu et al, "Imidacloprid and Related Compounds: Structure and Water Solubility of N-Alkyl Derivatives of Imidacloprid".
Reaktionen der organischen Synthese [Reaction of Organic Synthesis], C. Ferri, Georg Thieme Verlag Stuttgart (month unavailable) 1978, pp. 375-384, "Reaktionen zur Herstellung von Alkoholen, Phenolen und ihren Derivaten".
Reaktionen der organischen Synthese [Reaction of Organic Synthesis], C. Ferri, Georg Thieme Verlag Stuttgart (month unavailable) 1978, pp. 462-470, "Reaktionen zur Herstellung organischer Schwefel-Verbindungen".

(Continued)

*Primary Examiner*—Kamal A. Saeed
(74) *Attorney, Agent, or Firm*—Richard E. L. Henderson

(57) ABSTRACT

The present invention relates to novel halonitrobutadienes, to processes for their preparation and to their use for controlling animal pests.

5 Claims, No Drawings

OTHER PUBLICATIONS

Reaktionen der organischen Synthese [Reaction of Organic Synthesis], C. Ferri, Gerog Thieme Verlag Stuttgart (month unavailable) 1978, pp. 496-512, "Reaktionen zur Herstellung organischer Stickstoff-Verbindungen".

Organikum, Johann Ambrosius Barth Leipzig-Berlin-Heidelberg, Ed. Deutsbher Verlag der Wissenschaften, (date unavailable), pp. 228-229, "Allgemeine Arbeitsvorschift für die Veresterung von Alkoholen mit Bromwasserstoffsäure".

Database CA, Chemical Abstracts Service, Ibis, Cemil et al: "Synthesis of some new S-, S,S- and N,S-substituted 1,3-halonitrodienes" retrieved from STN Database accession No. 136: 101952 XP002228728 & Phosphorus, Sulfur and Silicon and the Related Elements (2001), 170, 221-231.

Database CA, Chemical Abstracts Service, Azarko, V.A. et al: "Film forming and spectral Properties of 2-nitro-3,4-dichloro-1,3-butadiene derivatives" Database accession No. 134:273423 XP002228729 & Vestsi Natsyyanal 'Nai Akademii Navuk Belarusi, Seryya Khimichnykh Navuk (2000), (4), 44-49.

Database CA, Chemical Abstracts Service, Vashkevich, E.V. et al: "Synthesis of trichloronitrodienamino adamantane derivatives", Database accession No. 133:120070 XP002228730 & Russian Journal of Organic Chemistry (Translation of Zhumal Organicheskoi Khimii) (1999), 35(12), 1773-1776.

Database CA, Chemical Abstracts Service, Zapol Skii, V.A. et al: "Azoly derivatives of nitrohalobutadienes. I. Reaction of 1,1-bis(benzotriazol-1-yl)-2-nitrotrihalo-1,3-butadienes with N-, N,N-, and N,O-nucleophiles", Database accession No. 129:189276, XP002228731 & Russian Journal of Organic Chemistry (Translation of Zhurnal Organicheskoi Khimii) (1997), 33(10), 1461-1467.

Database CA, Chemical Abstracts Service, Potkin, V.I. et al: "Synthesis and some reactions of 4-bromo-2-nitro-1,1,3,4-tetrachloro-1,3-butadiene", Database accession No. 125:113914 XP002228732 & Zhurnal Organicheskoi Khimii (1995), 31(12), 1816-1822.

Database CA, Chemical Abstracts Service, Zapol Skii, V.A. et al: "Synthesis of polyhalobutadienes and their functional derivatives from 1,2-dichloroethylene dimmer", Database accession No. 123:313100, XP002228733 & Zhurnal Organicheskoi Khimii (1994), 30(9), 1368-78.

Database CA, Chemical Abstracts Service, Zapolskii, V.A. et al: "Bromination of 1-bromo-1,4,4-trichloro-1,3-butadiene and some transformations of the obtained reaction products", Database accession No. 123:313088, XP002228734 & Zhurnal Organicheskoi (1994), 30(10), 1452-7.

Database CA, Chemical Abstracts Service, Zaplosky, V.A. et al: "Synthesis of dinitro-sub-stituted dienediamines from 1,3-dinitro-1,4,4-trichloro-1,3-butadiene", Database accession No. 122:104963, XP002228735 & Vestsi Akademii Navuk Belarusi, Seryya Khimichnykh Navuk (1994), (3), 82-4.

Database Chemcats, Chemical Abstracts Service, Database accession No. 2001:552236, XP002288803Order No. BAS 0432103 & "AslnEX Compound Collection" May 10, 2001, Asinex, 6 Schukinskaya Street Moscow, 123182, Russia.

Chem. Ind., 37, (month unavailable) 1985, pp. 730-732, Harry R. Ungerer, Schiffsfarben—eine Spezialität der seenahen Lackindustrie.

HALOGENATED NITROBUTADIENES FOR CONTROLLING ANIMAL PESTS

The present patent application has been filed under 35 U.S.C. 371 as a national stage application of PCT/EP02/11844, filed Oct. 23, 2002, which was published in German as International Patent Publication WO 03/040129 on May 15, 2003, which is entitled to the right of priority of German Patent Application 101 54 313.1, filed Nov. 5, 2001.

The present invention relates to novel unsaturated compounds, to processes for their preparation and to their use for controlling animal pests.

Various halogen-substituted 1,3-butadienes, such as, for example, 4-bromo-2-nitro-1,1,3,4-tetrachloro-1,3-butadiene (Yu. A. Ol'dekop et al., Zh. Org. Khim. 15, 6, 1979, pp. 1321-1322; V. I. Potkin et al., Zh. Org. Khim. 31, 2, 1995, pp. 1816-1822), 2-nitro-1,1,3,4,4-pentachloro-1,3-butadiene (Yu. A. Ol'dekop et al., Zh. Org. Khim. 12, 9, 1976, pp. 2039-2040; Potkin et al., Dokl. Nats. Akad. Nauk Belarusi 40, 1, 1996, pp. 68-71) or 1,3-dinitro-1,2,4,4-tetrachloro-1,3-butadiene (N. I. Nechai et al., Dokl. Nats. Akad. Nauk Belarusi 42, 2, 1989, pp. 75-78) are already known, and these compounds can be used as suitable starting materials in chemical synthesis (cf, for example, V. A. Zapol'ski et al., Russ. J. Org. Chem. 35, 3 1999, pp. 445-450).

It is also known that 1,1-bis(benzotriazol-1-yl)-, 1,1-bis(3,5-dimethylpyrazol-1-yl)- and 1,1-bis(1,2,4-triazol-1-yl)-2-nitrotrihalo-1,3-butadienes are highly reactive (cf. V. A. Zapol'ski et al., Russ. J. Org. Chem. 33, 10, 1997, pp. 1461-1467; V. A. Zapol'ski et al., Russ. J. Org. Chem. 33, 11, 1997, pp. 1632-1637).

Furthermore, trichloronitrodieneaminoadamantane derivatives, such as, for example, 1,1-bis-[1-(1-adamantyl)ethylamino]-3,4,4-trichloro-2-nitro-1,3-butadiene have already been described as compounds which have in vitro activity against tumours (cf. E. V. Vashkevich et al., Russ. J. Org. Chem. 35, 12, 1999, pp. 1773-1776).

However, nothing has hitherto been disclosed about the use of these compounds as crop protecting agents and, in particular, for controlling animal pests.

This invention now provides novel compounds of the formula (I)

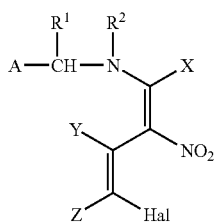

(I)

in which
A represents in each case optionally substituted cycloalkyl, heterocyclyl, aryl or hetaryl,
$R^1$ represents hydrogen or alkyl,
$R^2$ represents hydrogen or alkyl,
Z represents halogen or $NO_2$,
Hal represents halogen,
X represents $OR^3$, $SR^3$ or $NR^4R^5$,
Y represents hydrogen, halogen, $OR^6$, $SR^6$ or $NR^7R^8$,
$R^3$ represents in each case optionally substituted alkyl, alkenyl, cycloalkyl, cycloalkylalkyl, each of which is optionally interrupted by one or more heteroatoms, or represents in each case optionally substituted aryl, hetaryl, arylalkyl or hetarylalkyl,
$R^4$ and $R^5$ independently of one another represent hydrogen, represent in each case optionally substituted alkyl, alkenyl, alkynyl, cycloalkyl, cycloalkylalkyl, alkoxycarbonyl, each of which is optionally interrupted by one or more heteroatoms, or represent in each case optionally substituted aryl, hetaryl, arylalkyl or hetarylalkyl, or
$R^4$ and $R^5$ together with the nitrogen atom to which they are attached represent an optionally substituted ring which is optionally interrupted by one or more heteroatoms,
$R^6$ represents in each case optionally substituted alkyl, alkenyl, cycloalkyl, cycloalkylalkyl, each of which is optionally interrupted by one or more heteroatoms, or represents in each case optionally substituted aryl or arylalkyl,
$R^7$ and $R^8$ independently of one another represent in each case optionally substituted alkyl, alkenyl, cycloalkyl, cycloalkylalkyl, each of which is optionally interrupted by one or more heteroatoms, or represent in each case optionally substituted aryl, hetaryl, arylalkyl or hetarylalkyl, or
$R^7$ and $R^8$ together with the nitrogen atom to which they are attached represent an optionally substituted ring which is optionally interrupted by one or more heteroatoms, or
$R^2$ and $R^3$ together with the atoms linking them form an optionally substituted ring which is optionally interrupted by one or more heteroatoms, or
$R^2$ and $R^5$ together with the atoms linking them form an optionally substituted ring which is optionally interrupted by one or more heteroatoms.

Furthermore, it has been found that the compounds of the formula (I) according to the invention in which the radicals $R^2$ and $R^3$ or $R^2$ and $R^5$ together with the atoms linking them form a ring and Y represents hydrogen or chlorine are obtained when a compound of the formula (II)

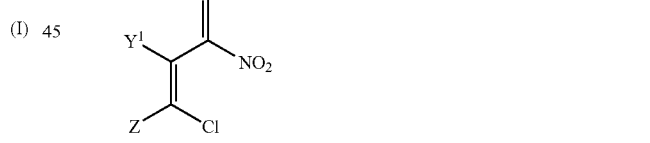

(II)

in which
$Y^1$ represents hydrogen or chlorine
Z represents chlorine, bromine or nitro are reacted with a compound of the formula (III)

(III)

in which
D represents in each case optionally substituted $—CH_2—CH_2—$ or $—CH_2—CH_2—CH_2—$, B represents OH, SH or

and
A and $R^1$ are as defined above, giving compounds of the formula (Ia)

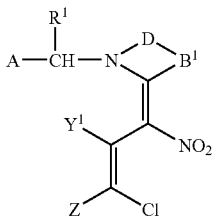

in which
A, $R^1$, D, $Y^1$ and Z are as defined above and
$B^1$ represents O, S or

Furthermore, compounds of the formula (Ib)

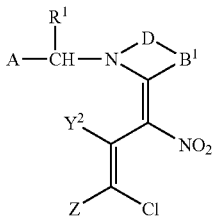

in which
A, $R^1$, D, $B^1$ and Z are as defined above and
$Y^2$ represents $OR^6$, $SR^6$ or $NR^7R^8$,
in which
$R^6$, $R^7$ and $R^8$ are as defined above, are obtained when compounds of the formula (Ia) in which $Y^1$ represents chlorine are reacted with compounds of the formula (IV)

 (IV)

in which
$Y^2$ is as defined above.

Alkyl, alone or as a component of a radical in the general formulae, denotes straight-chain or branched alkyl having preferably 1 to 6, in particular 1 to 4, carbon atoms. Methyl, ethyl, n-propyl, isopropyl, n-butyl, isobutyl, sec-butyl, tert-butyl, pentyl, 1-methylbutyl, 2-methylbutyl, 3-methylbutyl, 1,2-dimethylpropyl, 1,1-dimethylpropyl, 2,2-dimethylpropyl, 1-ethylpropyl, hexyl, 1-methylpentyl, 2-methylpentyl, 3-methylpentyl, 4-methylpentyl, 1,2-dimethylbutyl, 1,3-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1,2,2-trimethylpropyl, 1-ethylbutyl and ethylbutyl may be mentioned by way of example.

Methyl, ethyl, n-propyl, isopropyl, n-butyl, isobutyl, sec-butyl and tert-butyl may be mentioned as being preferred.

Alkenyl, alone or as a component of a radical in the general formulae, denotes straight-chain or branched alkenyl having preferably 2 to 6, in particular 2 to 4, carbon atoms. Vinyl, 2-propenyl, 2-butenyl, 3-butenyl, 1-methyl-2-propenyl, 2-methyl-2-propenyl, 2-pentenyl, 3-pentenyl, 4-pentenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-2-propenyl, 1-ethyl-2-propenyl, 2-hexenyl, 3-hexenyl, 4-hexenyl, 5-hexenyl, 1-methyl-2-pentenyl, 2-methyl-2-pentenyl, 3-methyl-2-pentenyl, 4-methyl-2-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-2-butenyl, 1,2-dimethyl-3-butenyl, 1,3-dimethyl-2-butenyl, 2,2-dimethyl-3-butenyl, 2,3-dimethyl-2-butenyl, 2,3-dimethyl-3-butenyl, 1-ethyl-2-butenyl, 1-ethyl-3-butenyl, 2-ethyl-2-butenyl, 2-ethyl-3-butenyl, 1,1,2-trimethyl-2-propenyl, 1-ethyl-1-methyl-2-propenyl and 1-ethyl-2-methyl-2-propenyl may be mentioned by way of example.

2-Propenyl, 2-butenyl and 1-methyl-2-propenyl may be mentioned as being preferred.

Alkynyl, alone or as a component of a radical in the general formulae, denotes straight-chain or branched alkynyl having preferably 2 to 6, in particular 3 or 4, carbon atoms. Optionally substituted 2-propynyl, 2-butynyl, 3-butynyl, 1-methyl-2-propynyl, 2-pentynyl, 3-pentynyl, 4-pentynyl, 1-methyl-3-butynyl, 2-methyl-3-butynyl, 1-methyl-2-butynyl, 1,1-dimethyl-2-propynyl, 1-ethyl-2-propynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-4-pentynyl, 4-methyl-2-pentynyl, 1,1-dimethyl-3-butynyl, 1,2-dimethyl-3-butynyl, 2,2-dimethyl-3-butynyl, 1-ethyl-3-butynyl, 2-ethyl-3-butynyl and 1-ethyl-1-methyl-2-propynyl may be mentioned by way of example.

2-Propynyl and 2-butynyl may be mentioned as being preferred.

Cycloalkyl, alone or as a component of a radical in the general formulae, denotes mono-, bi- and tricyclic cycloalkyl having preferably 3 to 10, in particular 3, 5 or 7 carbon atoms. Cyclopropyl, cyclobutyl, cyclopentyl, cyclohexyl, cycloheptyl, cyclooctyl, bicyclo[2.2.1]heptyl, bicyclo[2.2.2]octyl and adamantyl may be mentioned by way of example.

Haloalkyl, alone or as a component of a radical in the general formulae, contains 1 to 4, in particular 1 or 2, carbon atoms and preferably 1 to 9, in particular 1 to 5, identical or different halogen atoms, preferably fluorine, chlorine or bromine, in particular fluorine or chlorine. Trifluoromethyl, trichloromethyl, chlorodifluoromethyl, dichlorofluoromethyl, chloromethyl, bromomethyl, 1-fluoroethyl, 2-fluoroethyl, 2,2-difluoroethyl, 2,2,2-trifluoroethyl, 2,2,2-trichloroethyl, 2-chloro-2,2-difluoroethyl, pentafluoroethyl and pentafluoro-tert-butyl may be mentioned by way of example.

Alkoxy, alone or as a component of a radical in the general formulae, denotes straight-chain or branched alkoxy having preferably 1 to 6, in particular 1 to 4, carbon atoms.

Methoxy, ethoxy, n-propoxy, isopropoxy, n-butoxy, isobutoxy, sec-butoxy and tert-butoxy may be mentioned by way of example.

Alkoxyalkoxy, alone or as a component of a radical in the general formulae, denotes straight-chain or branched alkoxyalkoxy having preferably 2 to 6, in particular 2 to 4, carbon atoms. Optionally substituted methoxymethoxy, methoxyethoxy, methoxy-n-propoxy and ethoxyisopropoxy may be mentioned by way of example.

Alkoxyalkoxyalkoxy, alone or as a component of a radical in the general formulae, denotes straight-chain or branched alkoxyalkoxyalkoxy having preferably 3 to 6, in particular 3 or 4, carbon atoms. Methoxymethoxyethoxy, methoxyethoxyethoxy and methoxyethoxy-n-propoxy may be mentioned by way of example.

Haloalkoxy, alone or as a component of a radical in the general formulae, denotes straight-chain or branched haloalkoxy having preferably 1 to 6, in particular 1 to 4, carbon atoms. Optionally substituted difluoromethoxy, trifluoromethoxy, trichloromethoxy, chlorodifluoromethoxy, 1-fluoroethoxy, 2-fluoroethoxy, 2,2-difluoroethoxy, 1,1,2,2-tetrafluoroethoxy, 2,2,2-trifluoroethoxy and 2-chloro-1,1,2-trifluoroethoxy may be mentioned by way of example.

Alkylthio, alone or as a component of a radical in the general formulae, denotes straight-chain or branched alkylthio having preferably 1 to 6, in particular 1 to 4, carbon atoms. Methylthio, ethylthio, n-propylthio, isopropylthio, n-butylthio, isobutylthio, sec-butylthio and tert-butylthio may be mentioned by way of example.

Haloalkylthio, alone or as a component of a radical in the general formulae, denotes straight-chain or branched haloalkylthio having preferably 1 to 6, in particular 1 to 4, carbon atoms. Difluoromethylthio, trifluoromethylthio, trichloromethylthio, chlorodifluoromethylthio, 1-fluoroethylthio, 2-fluoroethylthio, 2,2-difluoroethylthio, 1,1,2,2-tetrafluoroethylthio, 2,2,2-trifluoroethylthio and 2-chloro-1,1,2-trifluoroethylthio may be mentioned by way of example.

Alkylcarbonyl, alone or as a component of a radical in the general formulae, denotes straight-chain or branched alkylcarbonyl having preferably 1 to 6, in particular 1 to 4, carbon atoms in the alkyl moiety. Optionally substituted methylcarbonyl, ethylcarbonyl, n-propylcarbonyl, isopropylcarbonyl, sec-butylcarbonyl and tert-butylcarbonyl may be mentioned by way of example.

Cycloalkylcarbonyl, alone or as a component of a radical in the general formulae, denotes mono-, bi- and tricyclic cycloalkylcarbonyl having preferably 3 to 10, in particular 3, 5 or 7, carbon atoms in the cycloalkyl moiety. Cyclopropylcarbonyl, cyclobutylcarbonyl, cyclobutylcarbonyl, cyclopentylcarbonyl, cyclohexylcarbonyl, cycloheptylcarbonyl, cyclooctylcarbonyl, bicyclo[2.2.1]heptylcarbonyl, bicyclo[2.2.2]octylcarbonyl and adamantylcarbonyl may be mentioned by way of example.

Alkoxycarbonyl, alone or as a component of a radical in the general formulae, denotes straight-chain or branched alkoxycarbonyl having preferably 1 to 6, in particular 1 to 4, carbon atoms in the alkoxy moiety. Methoxycarbonyl, ethoxycarbonyl, n-propoxycarbonyl, isopropoxycarbonyl, n-butoxycarbonyl, isobutoxycarbonyl, sec-butoxycarbonyl and tert-butoxycarbonyl may be mentioned by way of example.

Aryl is, for example, a mono-, di- or polycyclic aromatic radical, such as phenyl, naphthyl, tetrahydronaphthyl, indanyl, fluorenyl, preferably phenyl or naphthyl, in particular phenyl.

In the general formulae, arylalkyl preferably denotes arylalkyl having preferably 6 or 10, in particular 6, carbon atoms in the aryl moiety (preferably phenyl or naphthyl, in particular phenyl), and preferably 1 to 4, in particular 1 or 2, carbon atoms in the alkyl moiety, where the alkyl moiety may be straight-chain or branched and the aryl moiety and/or alkyl moiety is preferably optionally substituted. Benzyl and 1-phenylethyl may be mentioned by way of example and by way of preference.

The optionally substituted radicals of the general formulae may carry one or more, preferably 1 to 3, in particular 1 or 2, identical or different substituents. The following substituents may be mentioned by way of example and by way of preference:

Alkyl having preferably 1 to 4, in particular 1 or 2, carbon atoms, such as methyl, ethyl, n-propyl, isopropyl, n-butyl, isobutyl, sec-butyl and tert-butyl; alkoxy having preferably 1 to 4, in particular 1 or 2, carbon atoms, such as methoxy, ethoxy, n-propoxy, isopropoxy, n-butoxy, isobutoxy, sec-butoxy and tert-butoxy; alkylthio, such as methylthio, ethylthio, n-propylthio, isopropylthio, n-butylthio, isobutylthio, sec-butylthio; haloalkyl having preferably 1 to 5, in particular 1 to 3, halogen atoms, where the halogen atoms are identical or different and are preferably fluorine, chlorine or bromine, in particular fluorine or chlorine, such as difluoromethyl, trifluoromethyl, trichloromethyl; hydroxyl; halogen, preferably fluorine, chlorine, bromine and iodine, in particular fluorine and chlorine; cyano; nitro; amino; monoalkyl- and dialkylamino having preferably 1 to 4, in particular 1 or 2, carbon atoms per alkyl group, such as methylamino, methylethylamino, dimethylamino, n-propylamino, isopropylamino, methyl-n-butylamino; alkylcarbonyl radicals, such as methylcarbonyl; alkoxycarbonyl having preferably 2 to 4, in particular 2 or 3, carbon atoms, such as methoxycarbonyl and ethoxycarbonyl; alkylsulphinyl having 1 to 4, in particular 1 or 2, carbon atoms; haloalkylsulphinyl having 1 to 4, in particular 1 or 2, carbon atoms and 1 to 5 halogen atoms, such as trifluoromethylsulphinyl; haloalkylsulphonyl having 1 to 4, in particular 1 or 2, carbon atoms and 1 to 5 halogen atoms, such as trifluoromethylsulphonyl, perfluoro-n-butylsulphonyl, perfluoroisobutylsulphonyl; arylsulphonyl having preferably 6 or 10 aryl carbon atoms, such as phenylsulphonyl; acyl, aryl, aryloxy which for their part may carry one of the substituents mentioned above, and also the formimino radical (—HC=N—O-alkyl).

It is possible for two identical or different substituents to be present at the same atom.

In mono- or dialkylamino groups, alone or as a component of a radical in the general formulae, alkyl denotes straight-chain or branched alkyl having preferably 1 to 6, in particular 1 to 4, carbon atoms. Examples of substituted mono- or dialkylamino groups which may be mentioned are methylamino, ethylamino, dimethylamino, diethylamino, di-n-propylamino, diisopropylamino and dibutylamino.

In mono- or dialkoxyalkylamino groups, alone or as a component of a radical in the general formulae, alkoxyalkyl denotes straight-chain or branched alkoxyalkyl having preferably 2 to 6, in particular 2 to 4, carbon atoms. Examples of substituted mono- or dialkoxyalkylamino groups which may be mentioned are methoxymethylamino, methoxyethylamino, di(methoxymethyl)amino or di(methoxyethyl)amino.

Suitable cyclic amino groups are heteroaromatic or heteroaliphatic ring systems having one or more nitrogen atoms as heteroatom, where the heterocycles may be saturated or unsaturated, may comprise one ring system or a plurality of fused ring systems and may optionally contain further heteroatoms, such as, for example, one or two nitrogen, oxygen and sulphur, etc. Moreover, cyclic amino groups may also denote a spirocyclic ring or a bridged ring system. The number of atoms forming the cyclic amino groups is not limited, in the case of a one-ring system, for example, the ring may comprise 3 to 8 atoms and in the case of a three-ring system, the ring may comprise 7 to 11 atoms.

Examples of cyclic amino groups having saturated and unsaturated monocyclic groups and one nitrogen atom as heteroatom which may be mentioned are 1-azetidinyl, pyrrolidino, 2-pyrrolin-1-yl, 1-pyrrolyl, piperidino, 1,4-dihydropyrazin-1-yl, 1,2,5,6-tetrahydropyrazin-1-yl, 1,4-dihydropyridin-1-yl, 1,2,5,6-tetrahydropyridin-1-yl, homopiperidinyl; examples of cyclic amino groups having saturated and unsaturated monocyclic groups and two or more nitrogen atoms as heteroatoms which may be mentioned are 1-imidazolidinyl, 1-imidazolyl, 1-pyrazolyl, 1-triazolyl, 1-tetrazolyl, 1-piperazinyl, 1-homopiperazinyl, 1,2-dihydropyridazin-1-yl, 1,2-dihydropyrimidin-1-yl, perhydropyrimidin-1-yl, 1,4-diazacycloheptan-1-yl; examples of cyclic amino groups having saturated and unsaturated monocyclic groups and one or two oxygen atoms and one to three nitrogen atoms as heteroatoms which may be mentioned are oxazolidin-3-yl, 2,3-dihydroisoxazol-2-yl, isoxazol-2-yl, 1,2,3-oxadiazin-2-yl, morpholino; examples of cyclic amino groups having saturated and unsaturated monocyclic groups and one to three nitrogen atoms and one or two sulphur atoms as heteroatoms which may be mentioned are thiazolidin-3-yl, isothiazolin-2-yl, thiomorpholino or dioxothiomorpholino; examples of cyclic amino groups having saturated and unsaturated condensed cyclic groups which may be mentioned are indol-1-yl, 1,2-dihydrobenzimidazol-1-yl, perhydropyrrolo[1,2-a]-pyrazin-2-yl; an example of a cyclic amino group having spirocyclic groups which may be mentioned is 2-azaspiro[4,5]decan-2-yl; an example of a cyclic amino group having bridged heterocyclic groups which may be mentioned is 2-azabicyclo[2.2.1] heptan-7-yl.

The formula (I) provides a general definition of the compounds according to the invention.

Preferred substituents or ranges of the radicals listed in the formulae mentioned above and below are illustrated below.

A preferably represents optionally halogen- (fluorine-, chlorine-, bromine-), cyano-, nitro-, $C_1$-$C_4$-alkyl-, $C_1$-$C_4$-haloalkyl-, $C_1$-$C_4$-alkoxy- or $C_1$-$C_4$-haloalkoxy-substituted phenyl.

A furthermore preferably represents pyrazolyl, 1,2,4-triazolyl, oxazblyl, isoxazolyl, thiazolyl, isothiazolyl, 1,2,5-thiadiazolyl, pyridyl, pyrazinyl or pyrimidinyl, which are optionally substituted by fluorine, chlorine, bromine, cyano, nitro, $C_1$-$C_2$-alkyl (which is optionally substituted by fluorine and/or chlorine), $C_1$-$C_2$-alkoxy (which is optionally substituted by fluorine and/or chlorine), $C_1$-$C_2$-alkylthio (which is optionally substituted by fluorine and/or chlorine) or $C_1$-$C_2$-alkylsulphonyl (which is optionally substituted by fluorine and/or chlorine).

A furthermore preferably represents an optionally halogen- or $C_1$-$C_3$-alkyl-substituted saturated $C_5$-$C_6$-cycloalkyl radical in which optionally one methylene group is replaced by O or S.

$R^1$ preferably represents hydrogen, methyl, ethyl, n-propyl or i-propyl.

$R^2$ preferably represents hydrogen, methyl, ethyl, n-propyl or i-propyl.

Hal preferably represents bromine or chlorine.

X preferably represents $OR^3$, $SR^3$ or $NR^4R^5$.

Y preferably represents hydrogen, halogen (in particular chlorine), $OR^6$, $SR^6$ or $NR^7R^8$.

Z preferably represents bromine, chlorine or nitro.

$R^3$ preferably represents straight-chain or branched $C_1$-$C_6$-alkyl, $C_3$-$C_6$-alkenyl, $C_3$-$C_7$-cycloalkyl, $C_3$-$C_7$-cycloalkyl-$C_1$-$C_2$-alkyl, each of which is optionally interrupted by oxygen or sulphur and optionally substituted by halogen, hydroxyl or cyano, represents in each case optionally $C_1$-$C_4$-alkyl-, $C_1$-$C_2$-haloalkyl-, halogen-, $C_1$-$C_4$-alkoxy-, $C_1$-$C_2$-haloalkoxy-, nitro- or cyano-substituted phenyl-$C_1$-$C_2$-alkyl, phenyl, pyridyl, thiazolyl, pyrazolyl or pyrimidyl, or $R^2$ and $R^3$ preferably represent an optionally $C_1$-$C_4$-alkyl-substituted $C_2$-$C_4$-alkylidenediyl group.

$R^4$ and $R^5$ preferably and independently of one another represent hydrogen, represent straight-chain or branched $C_1$-$C_6$-alkyl, $C_3$-$C_6$-alkenyl, $C_3$-$C_6$-alkynyl, $C_3$-$C_7$-cycloalkyl, $C_3$-$C_7$-cycloalkyl-$C_1$-$C_6$-alkyl, $C_1$-$C_6$-alkoxycarbonyl, each of which is optionally interrupted by oxygen or sulphur and each of which is optionally substituted by halogen, or represent in each case optionally $C_1$-$C_4$-alkyl-, $C_1$-$C_2$-haloalkyl- or halogen-substituted phenyl, phenyl-$C_1$-$C_2$-alkyl, pyridyl, thiazolyl, pyridyl-$C_1$-$C_2$-alkyl or thiazolyl-$C_1$-$C_2$-alkyl.

$R^4$ and $R^5$ furthermore preferably together with the N atom to which they are attached represent a 4-, 5-, 6- or 7-membered ring or represent a 7- to 10-membered bicycle which are optionally interrupted by oxygen, sulphur, sulphoxyl, sulphonyl, carbonyl, N—$R^6$ or by quaternized nitrogen and optionally substituted by $C_1$-$C_4$-alkyl, or $R^2$ and $R^5$ preferably together with the atoms linking them represent an optionally $C_1$-$C_4$-alkyl-substituted saturated 5-, 6- or 7-membered ring which, in addition to the two nitrogen atoms, contains no further heteroatoms.

$R^6$ preferably represents straight-chain or branched $C_1$-$C_6$-alkyl, $C_3$-$C_6$-alkenyl, $C_5$-$C_7$-cycloalkyl, $C_3$-$C_7$-cycloalkyl-$C_1$-$C_2$-alkyl, each of which is optionally interrupted by oxygen or sulphur and optionally substituted by fluorine or chlorine, or represents in each case optionally halogen-, $C_1$-$C_4$-alkyl-, $C_1$-$C_4$-alkoxy-, $C_1$-$C_2$-haloalkyl-, $C_1$-$C_2$-haloalkoxy-, nitro- or cyano-substituted phenyl-$C_1$-$C_4$-alkyl, pyridyl, thiazolyl-$C_1$-$C_2$-alkyl, phenyl, pyridyl, pyrimidyl, thiazolyl.

$R^7$ and $R^8$ preferably and independently of one another represent straight-chain or branched $C_1$-$C_6$-alkyl, $C_3$-$C_6$-alkenyl, $C_3$-$C_7$-cycloalkyl, $C_3$-$C_7$-cycloalkyl-$C_1$-$C_6$-alkyl, each of which is optionally interrupted by oxygen or sulphur and optionally substituted by fluorine or chlorine, represent in each case optionally $C_1$-$C_4$-alkyl-, $C_1$-$C_4$-alkoxy-, halogen-, $C_1$-$C_2$-haloalkyl-, $C_1$-$C_4$-haloalkoxy-, nitro- or cyano-substituted phenyl or phenyl-$C_1$-$C_2$-alkyl.

$R^7$ and $R^8$ furthermore preferably together with the N atom to which they are attached represent a 4-, 5-, 6- or 7-membered ring or represent a 7- to 11-membered bicycle which are optionally also interrupted by oxygen, sulphur, sulphoxyl, sulphonyl, carbonyl, —N—$R^6$ or by quaternized nitrogen and optionally substituted by $C_1$-$C_4$-alkyl.

A particularly preferably represents thiazolyl or pyridyl which are in each case optionally substituted by halogen (in particular chlorine) or $C_1$-$C_3$-alkyl (in particular methyl).

A furthermore particularly preferably represents an optionally halogen- (in particular chlorine-) or $C_1$-$C_3$-alkyl- (in particular methyl-) substituted tetrahydrofuryl radical.

R¹ particularly preferably represents hydrogen or methyl.
R² particularly preferably represents hydrogen, methyl or ethyl.
Hal particularly preferably represents bromine or chlorine.
X particularly preferably represents SR³ or NR⁴R⁵.
Y particularly preferably represents hydrogen, chlorine, SR⁶ or NR⁷R⁸.
Z particularly preferably represents chlorine or nitro.
R³ particularly preferably represents straight-chain or branched C₁-C₄-alkyl, in particular methyl, ethyl, propyl, isopropyl, isobutyl, sec-butyl, tert-butyl, hydroxy-C₁-C₄-alkyl, in particular 2-hydroxyethyl, 3-hydroxypropyl, C₃-C₄-alkenyl, in particular 2-propenyl, 2-butenyl, C₅-C₇-cycloalkyl, in particular cyclopentyl, cyclohexyl, C₃-C₇-cycloalkyl-C₁-C₂-alkyl, in particular cyclopropylmethyl, in each case optionally fluorine-, chlorine-, bromine-, C₁-C₄-alkyl-, C₁-C₄-alkoxy-, C₁-C₂-haloalkyl-, C₁-C₂-haloalkoxy-, nitro- or cyano-substituted phenyl or benzyl, or
R² and R³ particularly preferably represent a C₂-C₃-alkylidenediyl group.
R⁴ and R⁵ particularly preferably and independently of one another represent hydrogen, straight-chain or branched C₁-C₄-alkyl or C₁-C₄-haloalkyl, in particular methyl, ethyl, propyl, isopropyl, trifluoroethyl, 1,1,1-trifluoroisopropyl, C₃-C₄-alkenyl, in particular 2-propenyl, 2-butenyl.
R⁴ and R⁵ furthermore particularly preferably represent C₄-C₆-alkylidenediyl which is optionally substituted by methyl or ethyl and optionally interrupted by oxygen, sulphur or N—R⁶, and in particular together with the N atom to which they are attached represent pyrrolidino, morpholino, thiomorpholino, piperidino, imidazolo or piperazino, or
R² and R⁵ particularly preferably together with the atoms linking them represent a saturated 5-, 6- or 7-membered ring which, in addition to the two nitrogen atoms, contains no further heteroatoms.
R⁶ particularly preferably represents straight-chain or branched C₁-C₄-alkyl, in particular methyl, ethyl, propyl, isopropyl, n-butyl, isobutyl, sec-butyl, tert-butyl, allyl, or represents in each case optionally fluorine-, chlorine-, bromine-, C₁-C₄-alkyl-, C₁-C₂-alkoxy-, trifluoromethyl-, trifluoromethoxy-, cyano- or nitro-substituted phenyl or benzyl.
R⁷ and R⁸ particularly preferably and independently of one another represent straight-chain or branched C₁-C₄-alkyl, in particular methyl, ethyl, propyl, isopropyl, butyl, isobutyl, sec-butyl, tert-butyl, C₃-C₄-alkenyl, in particular 2-propenyl, 2-butenyl, C₃-C₇-cycloalkyl, in particular cyclopropyl, cyclobutyl, cyclopentyl, cyclohexyl or cycloheptyl, C₃-C₇-cycloalkyl-C₁-C₂-alkyl, in particular cyclopropylmethyl, cyclobutylmethyl, cyclopentylmethyl, cyclohexylmethyl or cycloheptylmethyl, or represent in each case optionally nitro-, cyano-, halogen-, in particular bromine-, chlorine- or fluorine-, C₁-C₄-alkyl-, in particular methyl-, C₁-C₄-haloalkyl-, in particular trifluoromethyl-, C₁-C₄-alkoxy-, in particular methoxy-, or halo-C₁-C₂-alkoxy-, in particular trifluoromethoxy-, substituted phenyl or benzyl.
R⁷ and R⁸ furthermore particularly preferably together with the N atom to which they are attached represent a 5-, 6- or 7-membered ring or represent a 7- to 11-membered bicycle which are optionally also interrupted by oxygen, sulphur, carbonyl, N-methyl, N-ethyl, N-allyl, N-phenyl, N-chlorophenyl, N-benzyl and optionally substituted by methyl or ethyl.

A very particularly preferably represents one of the radicals

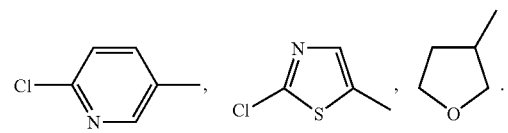

R¹ very particularly preferably represents hydrogen or methyl.
R² very particularly preferably represents hydrogen or methyl.
Hal very particularly preferably represents bromine or chlorine, in particular chlorine.
X very particularly preferably represents SR³ or NR⁴R⁵.
Y very particularly preferably represents chlorine, SR⁶ or NR⁷R⁸.
Z very particularly preferably represents chlorine.
R³ very particularly preferably represents methyl or phenyl.
R² and R³ very particularly preferably represent a C₂-C₃-alkylidenediyl group.
R⁴ and R⁵ very particularly preferably and independently of one another represent hydrogen, methyl or ethyl, or
R² and R⁵ very particularly preferably together with the atoms linking them represent a saturated 5- or 6-membered ring which, in addition to the two nitrogen atoms, contains no further heteroatoms.
R⁶ very particularly preferably represents straight-chain or branched C₁-C₄-alkyl, in particular methyl, ethyl, propyl, isopropyl, isobutyl, sec-butyl, tert-butyl, allyl or represents in each case optionally fluorine-, chlorine-, bromine-, methyl-, ethyl-, isopropyl-, tert-butyl-, methoxy-, trifluoromethyl-, trifluoromethoxy-, cyano- or nitro-substituted phenyl or benzyl.
R⁷ and R⁸ very particularly preferably and independently of one another represent straight-chain or branched C₁-C₄-alkyl, in particular methyl, ethyl, propyl, isopropyl, isobutyl, sec-butyl, tert-butyl, C₃-C₄-alkenyl, in particular 2-propenyl, 2-butenyl, C₃-C₇-cycloalkyl, in particular cyclopropyl, cyclobutyl, cyclopentyl, cyclohexyl or cycloheptyl, C₃-C₇-cycloalkyl-C₁-C₂-alkyl, in particular cyclopropylmethyl, cyclopentylmethyl or cyclohexylmethyl, phenyl-C₁-C₂-alkyl, nitro, or represent in each case optionally cyano-, methyl-, ethyl-, isopropyl-, tert-butyl-, bromine-, chlorine-, fluorine- or trifluoromethoxy-substituted phenyl or benzyl.
R⁷ and R⁸ furthermore very particularly preferably together with the N atom to which they are attached represent a 5-, 6- or 7-membered ring or represent a 7- to 11-membered bicycle which are optionally also interrupted by oxygen, sulphur, carbonyl, N-methyl, N-ethyl, N-allyl, N-phenyl, N-chlorophenyl, N-benzyl and optionally substituted by methyl.

In a particular group of compounds of the formula (I), A represents

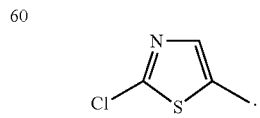

In a further particular group of compounds of the formula (I), A represents

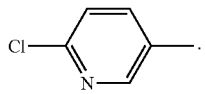

In a further particular group of compounds of the formula (I), A represents

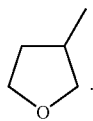

In a further group of particular compounds, $R^1$ represents hydrogen.

In a further group of particular compounds, Z represents chlorine.

In a further group of particular compounds, Hal represents chlorine.

In a further particular group of compounds of the formula (I),
$R^2$ and X represent a radical —$CH_2$—$CH_2$—S—.

In a further particular group of compounds of the formula (I),
$R^2$ and X represent a radical —$CH_2$—$CH_2$—NH—.

In a further particular group of compounds of the formula (I),
$R^2$ and X represent a radical —$CH_2$—$CH_2$—$CH_2$—S—.

In a further particular group of compounds of the formula (I),
$R^2$ and X represent a radical —$CH_2$—$CH_2$—$CH_2$—NH—.

In a further particular group of compounds of the formula (I), Y represents $NR^7R^8$ and
$R^7$ and $R^8$ together with the nitrogen atom to which they are attached represent a 5-, 6- or 7-membered ring which is optionally interrupted by oxygen, sulphur or N—$R^6$.

The general or preferred radical definitions or illustrations listed above apply both to the end products and, correspondingly, to starting materials and intermediates. These radical definitions can be combined with one another as desired, i.e. including combinations between the respective preferred ranges.

Preference according to the invention is given to compounds of the formula (I) which contain a combination of the meanings listed above as being preferred.

Particular preference according to the invention is given to the compounds of the formula (I) which contain a combination of the meanings listed above as being particularly preferred.

Very particular preference according to the invention is given to the compounds of the formula (I) which contain a combination of the meanings listed above as being very particularly preferred.

In the radical definitions given above and below, hydrocarbon radicals, such as alkyl, are in each case straight-chain or branched as far as this is possible—including in combination with heteroatoms, such as in alkoxy.

The compounds of the general formula (I) are novel; they can be prepared, for example, by the processes given above.

Below, the processes according to the invention are illustrated using selected examples (cf. also the Preparation Examples).

If, in the process according to the invention for preparing the novel unsaturated compounds of the general formula (Ia), 2-nitro-1,1,3,4,4-pentachloro-1,3-butadiene is used as compound of the general formula (II) and N-(6-chloropyridin-3-ylmethyl)-ethylene-1,2-diamine ($R^1$: 2-chloropyrid-5-yl; A: —H; D: —$CH_2$—$CH_2$—; B: —$NH_2$) is used as amino compound of the general formula (III), the process can be represented by reaction scheme I below:

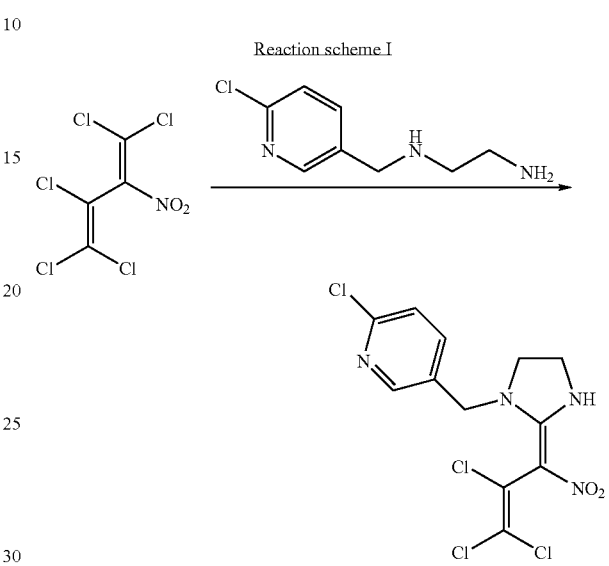

Reaction scheme I

If halogen-substituted 1,3-butadienes of the general formula (II) are used, the process according to the invention may, if appropriate, afford the compounds of the general formula (I) as a mixture of E and Z isomers.

The formula (II) provides a general definition of the halogen-substituted 1,3-butadienes required as starting materials for carrying out the process according to the invention.

The halogen-substituted 1,3-butadienes used as starting materials are known (cf. Yu. A. Ol'dekop et al., Zh. Org. Khim. 15, 6, 1979, p. 1321-1322; V. I. Potkin et al., Zh. Org. Khim. 31, 2, 1995, p. 1816-1822; Yu. A. Ol'dekop et al., Zh. Org. Khim. 12, 9, 1976, p. 2039-2040; Potkin et al., Dokl. Nats. Akad. Nauk Belarusi 40, 1, 1996, p. 68-71; N. I. Nechai et al., Dokl. Nats. Akad. Nauk Belarusi 42, 2, 1998, p. 75-78).

The general formula (III) provides a definition of the compounds furthermore to be used as starting materials for carrying out the process according to the invention.

In this formula (III), A, B, D and $R^1$ are as defined above.

Some of the compounds of the general formula (III) are known, and they can be obtained by known methods (cf., for example, hydroxy compounds where B=OH: EP 192060; mercapto compounds where B=SH: Jap-Pat. 05070431; amino compounds where B=$NHR^4$: DE-A 19710613, JP-Pat. 07242633, JP-Pat. 06016636, JP-Pat. 05310697, JP-Pat. 04217957, EP 609811, EP 542086, EP 474057, EP 163855; S. Kagabu et al., Biosci., Biotechnol., Biochem. 62, 6, 1998, p. 1216-1224).

In general, it is advantageous to carry out the reaction of the halogen-substituted 1,3-butadienes of the general formula (II) with the compounds of the general formula (III) in the presence of diluents. Diluents are advantageously employed in such an amount that the reaction mixture remains readily stirrable during the entire process. Suitable diluents for carrying out the process according to the invention are all organic solvents which are inert to the reactants.

Examples which may be mentioned are: halogenated hydrocarbons, in particular chlorinated hydrocarbons, such as tetrachloroethylene, tetrachloroethane, dichloropropane, methylene chloride, dichlorobutane, chloroform, carbon tetrachloride, trichloroethane, trichloroethylene, pentachloroethane, difluorobenzene, 1,2-dichloroethane, chlorobenzene, bromobenzene, dichlorobenzene, chlorotoluene, trichlorobenzene; alcohols, such as methanol, ethanol, isopropanol, tert-butanol; ethers, such as ethyl propyl ether, methyl tert-butyl ether, methyl-n-butyl ether, anisole, phenetol, cyclohexyl methyl ether, dimethyl ether, diethyl ether, dipropyl ether, diisopropyl ether, di-n-butyl ether, diisobutyl ether, diisoamyl ether, ethylene glycol dimethyl ether, tetrahydrofuran, dioxane, dichlorodiethyl ether and polyethers of ethylene oxide and/or propylene oxide; nitrohydrocarbons, such as nitromethane, nitroethane, nitropropane, nitrobenzene, chloronitrobenzene, o-nitrotoluene; nitriles, such as acetonitrile, propionitrile, butyronitrile, isobutyronitrile, benzonitrile, m-chlorobenzonitrile, and also compounds such as tetrahydrothiophene dioxide and dimethyl sulphoxide, tetramethylene sulphoxide, dipropyl sulphoxide, benzyl methyl sulphoxide, diisobutyl sulphoxide, dibutyl sulphoxide, diisoamyl sulphoxide; sulphones, such as dimethyl sulphone, diethyl sulphone, dipropyl sulphone, dibutyl sulphone, diphenyl sulphone, dihexyl sulphone, methyl ethyl sulphone, ethyl propyl sulphone, ethyl isobutyl sulphone and pentamethylene sulphone; aliphatic, cycloaliphatic or aromatic hydrocarbons, such as pentane, hexane, heptane, octane, nonane and technical-grade hydrocarbons, for example white spirits with components having boiling points in the range of, for example, from 40° C. to 250° C., cymene, petroleum fractions having a boiling point in the range from 70° C. to 190° C., cyclohexane, methylcyclohexane, petroleum ether, ligroin, octane, benzene, toluene, chlorobenzene, bromobenzene, nitrobenzene, xylene; esters, such as methyl acetate, ethyl acetate, butyl acetate, isobutyl acetate, and also dimethyl carbonate, dibutyl carbonate, ethylene carbonate; amides, such as hexamethylphosphoric triamide, formamide, N-methylformamide, N,N-dimethylacetamide, N,N-dimethylformamide, N,N-dipropylformamide, N,N-dibutylformamide, N-methylpyrrolidone, N-methylcaprolactam, 1,3-dimethyl-3,4,5,6-tetrahydro-2(1H)-pyrimidine, octylpyrrolidone, octylcaprolactam, 1,3-dimethyl-2-imidazolinedione, N-formylpiperidine, N,N'-1,4-diformylpiperazine; ketones, such as acetone, acetophenone, methyl ethyl ketone, methyl butyl ketone.

The process according to the invention can of course also be carried out using mixtures of the solvents and diluents mentioned.

However, preferred diluents for carrying out the process according to the invention are nitriles, such as acetonitrile, propionitrile, butyronitrile or isobutyronitrile, in particular acetonitrile or propionitrile, esters, such as methyl acetate, ethyl acetate, butyl acetate, isobutyl acetate, in particular methyl acetate and ethyl acetate, amides, such as N,N-dimethylformamide, N,N-dimethylacetamide, N,N-dipropylformamide, N,N-dibutylformamide, N-methylpyrrolidone, in particular N,N-dimethylformamide, N,N-dimethylacetamide and N-methylpyrrolidone, alcohols, such as methanol, ethanol, isopropanol, tert-butanol, in particular methanol, ethers, such as ethyl propyl ether, methyl tert-butyl ether, cyclohexyl methyl ether, dimethyl ether, diethyl ether, diisopropyl ether, tetrahydrofuran, dioxane, in particular methyl tert-butyl ether, tetrahydrofuran and dioxane, and also dimethyl sulphoxide.

The conversion of compounds of the general formula (II) by the process according to the invention is carried out by reacting the halogen-substituted 1,3-butadienes of the general formula (II) in the presence of a compound of the general formula (III) in one of the diluents stated.

The reaction time is from 10 minutes to 48 hours. The reaction is carried out at temperatures between −100° C. and +70° C., preferably between −78° C. and +50° C., particularly preferably between −50° C. and +30° C. In principle, it is possible to operate under atmospheric pressure. The reaction is preferably carried out under atmospheric pressure and, if appropriate, under an atmosphere of protective gas (nitrogen or argon). However, it is also possible to operate under elevated pressure.

For carrying out the process according to the invention, in general from 0.5 to 4.0 mol, preferably from 1.0 to 3.5 mol, particularly preferably from 1.5 to 2.5 mol, of a compound of the general formula (III) are employed per mole of halogen-substituted 1,3-butadiene of the general formula (II).

After the reaction is ended, the reaction products are separated in a customary manner. They can be purified by recrystallization, vacuum distillation or column chromatography (cf. also the Preparation Examples).

If, in the processes according to the invention for preparing the novel unsaturated compounds of the general formula (Ib), the compound of the general formula (Ia) used is the 2-chloro-5-[2-(2,3,3-trichloro-1-nitroallylidene)imidazolidin-1-ylmethyl]-pyridine obtained beforehand and the amino compound of the general formula (IV) used is thiomorpholine ($Y^2$: $NR^7R^8$, where $R^7$-$R^8$: —$CH_2$—$CH_2$—S—$CH_2$—$CH_2$), the process can be represented by reaction scheme II below:

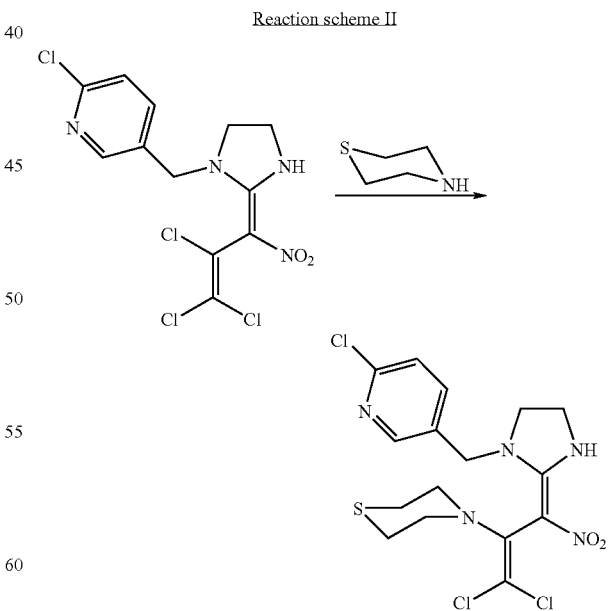

Reaction scheme II

If halogen-substituted 1,3-butadienes of the general formula (Ia) are used, the process according to the invention may, if appropriate, afford the compounds of the general formula (Ib) as a mixture of E and Z isomers.

The formula (Ia) provides a general definition of the halogen-substituted 1,3-butadienes required as starting materials for carrying out the process according to the invention.

In this formula (Ia), $Y^1$ represents halogen, in particular chlorine.

The halogen-substituted 1,3-butadienes used as starting materials can be obtained by the process mentioned above.

The general formula (IV) provides a definition of the compounds furthermore to be used as starting materials for carrying out the process according to the invention.

Some of the compounds of the general formula (IV) are known, some are commercially available, and they can be prepared by known methods (cf., for example, reactions for preparing alcohols, sulphur compounds and organic nitrogen compounds in "Reaktionen der organischen Synthese" [Reactions of Organic Synthesis], C. Ferri, Georg Thieme Verlag Stuttgart 1978, p. 375-384; p. 462-468 and p. 496-512; Organikum, Johann Ambrosius Barth Leipzig-Berlin-Heidelberg, Ed. Deutscher Verlag der Wissenschaften, Literature references on p. 228 and p. 229).

In general, it is advantageous to carry out the reaction of the compounds of the general formula (Ia) with the compounds of the general formula (IV) in the presence of diluents. Diluents are preferably employed in such an amount that the reaction mixture remains readily stirrable during the entire process. Suitable diluents for carrying out the process according to the invention are all of the inert organic solvents mentioned above.

However, preferred diluents for carrying out the process according to the invention are nitriles, such as acetonitrile, propionitrile, butyronitrile, isobutyronitrile, in particular acetonitrile or propionitrile, amides, such as N,N-dimethylformamide, N,N-dimethylacetamide, N,N-dipropylformamide, N,N-dibutylformamide, N-methylpyrrolidone, in particular N,N-dimethylformamide, N,N-dimethylacetamide and N-methylpyrrolidone, alcohols, such as methanol, ethanol, isopropanol, tert-butanol, in particular methanol, and also dimethyl sulphoxide.

The reaction of compounds of the general formula (Ia) by the process according to the invention is carried out by reacting the compounds of the general formula (Ia) in the presence of a compound of the general formula (IV) in one of the diluents mentioned.

The reaction time is from 10 minutes to 48 hours. The reaction is carried out at temperatures between −70° C. and +200° C., preferably between −30° C. and +150° C., particularly preferably between 0° C. and +100° C. In principle, it is possible to operate under atmospheric pressure. The process is preferably carried out under atmospheric pressure and, if appropriate, under an atmosphere of protective gas (nitrogen or argon). However, it is also possible to operate under elevated pressure.

For carrying out the process according to the invention, in general from 1.0 to 5.0 mol, preferably from 1.5 to 4.5 mol, particularly preferably from 2.0 to 3.5 mol, of a compound of the general formula (V) are employed per mole of halogen-substituted 1,3-butadiene of the general formula (Ia).

After the reaction is ended, the reaction products are separated in a customary manner. They can be purified in a customary manner by recrystallization, vacuum distillation or column chromatography (cf. also the Preparation Examples).

The active compounds are suitable for controlling animal pests, in particular insects, arachnids and nematodes, which are encountered in agriculture, in forestry, in the protection of stored products and of materials, and in the hygiene sector, and have good plant tolerance and favourable toxicity to warm-blooded animals. They may preferably be employed as plant protection agents. They are active against normally sensitive and resistant species and against all or some stages of development. The above-mentioned pests include:

From the order of the Isopoda, for example, *Oniscus asellus*, *Armadillidium vulgare* and *Porcellio scaber*.

From the order of the Diplopoda, for example, *Blaniulus guttulatus*.

From the order of the Chilopoda, for example, *Geophilus carpophagus* and *Scutigera* spp.

From the order of the Symphyla, for example, *Scutigerella immaculata*.

From the order of the Thysanura, for example, *Lepisma saccharina*.

From the order of the Collembola, for example, *Onychiurus armatus*.

From the order of the Orthoptera, for example, *Acheta domesticus*, *Gryllotalpa* spp., *Locusta migratoria migratorioides*, *Melanoplus* spp. and *Schistocerca gregaria*.

From the order of the Blattaria, for example, *Blatta orientalis*, *Periplaneta americana*, *Leucophaea maderae* and *Blattella germanica*.

From the order of the Dermaptera, for example, *Forficula auricularia*.

From the order of the Isoptera, for example, *Reticulitermes* spp.

From the order of the Phthiraptera, for example, *Pediculus humanus corporis*, *Haematopinus* spp., *Linognathus* spp., *Trichodectes* spp. and *Damalinia* spp.

From the order of the Thysanoptera, for example, *Hercinothrips femoralis*, *Thrips tabaci*, *Thrips palmi* and *Frankliniella occidentalis*.

From the order of the Heteroptera, for example, *Eurygaster* spp., *Dysdercus intermedius*, *Piesma quadrata*, *Cimex lectularius*, *Rhodnius prolixus* and *Triatoma* spp.

From the order of the Homoptera, for example, *Aleurodes brassicae*, *Bemisia tabaci*, *Trialeurodes vaporariorum*, *Aphis gossypii*, *Brevicoryne brassicae*, *Cryptomyzus ribis*, *Aphis fabae*, *Aphis pomi*, *Eriosoma lanigerum*, *Hyalopterus arundinis*, *Phylloxera vastatrix*, *Pemphigus* spp., *Macrosiphum avenae*, *Myzus* spp., *Phorodon humuli*, *Rhopalosiphum padi*, *Empoasca* spp., *Euscelis bilobatus*, *Nephotettix cincticeps*, *Lecanium corni*, *Saissetia oleae*, *Laodelphax striatellus*, *Nilaparvata lugens*, *Aonidiella aurantii*, *Aspidiotus hederae*, *Pseudococcus* spp. and *Psylla* spp.

From the order of the Lepidoptera, for example, *Pectinophora gossypiella*, *Bupalus piniarius*, *Cheimatobia brumata*, *Lithocolletis blancardella*, *Hyponomeuta padella*, *Plutella xylostella*, *Malacosoma neustria*, *Euproctis chrysorrhoea*, *Lymantria* spp., *Bucculatrix thurberiella*, *Phyllocnistis citrella*, *Agrotis* spp., *Euxoa* spp., *Feltia* spp., *Earias insulana*, *Heliothis* spp., *Mamestra brassicae*, *Panolis flammea*, *Spodoptera* spp., *Trichoplusia ni*, *Carpocapsa pomonella*, *Pieris* spp., *Chilo* spp., *Pyrausta nubilalis*, *Ephestia kuehniella*, *Galleria mellonella*, *Tineola bisselliella*, *Tinea pellionella*, *Hofmannophila pseudospretella*, *Cacoecia podana*, *Capua reticulana*, *Choristoneura fumiferana*, *Clysia ambiguella*, *Homona magnanima*, *Tortrix viridana*, *Cnaphalocerus* spp. and *Oulema oryzae*.

From the order of the Coleoptera, for example, *Anobium punctatum*, *Rhizopertha dominica*, *Bruchidius obtectus*, *Acanthoscelides obtectus*, *Hylotrupes bajulus*, *Agelastica alni*, *Leptinotarsa decemlineata*, *Phaedon cochleariae*, *Diabrotica* spp., *Psylliodes chrysocephala*, *Epilachna*

*varivestis, Atomaria* spp., *Oryzaephilus surinamensis, Anthonomus* spp., *Sitophilus* spp., *Otiorrhynchus sulcatus, Cosmopolites sordidus, Ceuthorrhynchus assimilis, Hypera postica, Dermestes* spp., *Trogoderma* spp., *Anthrenus* spp., *Attagenus* spp., *Lyctus* spp., *Meligethes aeneus, Ptinus* spp., *Niptus hololeucus, Gibbium psylloides, Tribolium* spp., *Tenebrio molitor, Agriotes* spp., *Conoderus* spp., *Melolontha melolontha, Amphimallon solstitialis, Costelytra zealandica* and *Lissorhoptrus oryzophilus*.

From the order of the Hymenoptera, for example, *Diprion* spp., *Hoplocampa* spp., *Lasius* spp., *Monomorium pharaonis* and *Vespa* spp.

From the order of the Diptera, for example, *Aedes* spp., *Anopheles* spp., *Culex* spp., *Drosophila melanogaster, Musca* spp., *Fannia* spp., *Calliphora erythrocephala, Lucilia* spp., *Chrysomyia* spp., *Cuterebra* spp., *Gastrophilus* spp., *Hyppobosca* spp., *Stomoxys* spp., *Oestrus* spp., *Hypoderma* spp., *Tabanus* spp., *Tannia* spp., *Bibio hortulanus, Oscinella frit, Phorbia* spp., *Pegomyia hyoscyami, Ceratitis capitata, Dacus oleae, Tipula paludosa, Hylemyia* spp. and *Liriomyza* spp.

From the order of the Siphonaptera, for example, *Xenopsylla cheopis* and *Ceratophyllus* spp.

From the class of the Arachnida, for example, *Scorpio maurus, Latrodectus mactans, Acarus siro, Argas* spp., *Ornithodoros* spp., *Dermanyssus gallinae, Eriophyes ribis, Phyllocoptruta oleivora, Boophilus* spp., *Rhipicephalus* spp., *Amblyomma* spp., *Hyalomma* spp., *Ixodes* spp., *Psoroptes* spp., *Chorioptes* spp., *Sarcoptes* spp., *Tarsonemus* spp., *Bryobia praetiosa, Panonychus* spp., *Tetranychus* spp., *Hemitarsonemus* spp. and *Brevipalpus* spp.

The phytoparasitic nematodes include, for example, *Pratylenchus* spp., *Radopholus similis, Ditylenchus dipsaci, Tylenchulus semipenetrans, Heterodera* spp., *Globodera* spp., *Meloidogyne* spp., *Aphelenchoides* spp., *Longidorus* spp., *Xiphinema* spp., *Trichodorus* spp. and *Bursaphelenchus* spp.

If appropriate, the compounds according to the invention can, at certain concentrations or application rates, also be used as herbicides or microbicides, for example as fungicides, antimycotics and bactericides. If appropriate, they can also be employed as intermediates or precursors for the synthesis of other active compounds.

All plants and plant parts can be treated in accordance with the invention. Plants are to be understood as meaning in the present context all plants and plant populations such as desired and undesired wild plants or crop plants (including naturally occurring crop plants). Crop plants can be plants which can be obtained by conventional plant breeding and optimization methods or by biotechnological and recombinant methods or by combinations of these methods, including the transgenic plants and including the plant cultivars protectable or not protectable by plant breeders' rights. Plant parts are to be understood as meaning all parts and organs of plants above and below the ground, such as shoot, leaf, flower and root, examples which may be mentioned being leaves, needles, stalks, stems, flowers, fruit bodies, fruits and seeds and also roots, tubers and rhizomes. The plant parts also include harvested material, and vegetative and generative propagation material, for example cuttings, tubers, rhizomes, offshoots and seeds.

The treatment according to the invention of the plants and plant parts with the active compounds is carried out directly or by allowing the compounds to act on the surroundings, environment or storage space by the customary treatment methods, for example by immersion, spraying, evaporation, fogging, scattering, painting on and, in the case of propagation material, in particular in the case of seeds, also by applying one or more coats.

The active compounds can be converted into the customary formulations, such as solutions, emulsions, wettable powders, suspensions, powders, dusts, pastes, soluble powders, granules, suspension-emulsion concentrates, natural and synthetic materials impregnated with active compound and microencapsulations in polymeric substances.

These formulations are produced in a known manner, for example by mixing the active compounds with extenders, that is to say liquid solvents and/or solid carriers, optionally with the use of surfactants, that is to say emulsifiers and/or dispersants and/or foam-formers.

If the extender used is water, it is also possible to employ for example organic solvents as auxiliary solvents. Essentially, suitable liquid solvents are: aromatics such as xylene, toluene or alkylnaphthalenes, chlorinated aromatics and chlorinated aliphatic hydrocarbons such as chlorobenzenes, chloroethylenes or methylene chloride, aliphatic hydrocarbons such as cyclohexane or paraffins, for example petroleum fractions, mineral and vegetable oils, alcohols such as butanol or glycol and also their ethers and esters, ketones such as acetone, methyl ethyl ketone, methyl isobutyl ketone or cyclohexanone, strongly polar solvents such as dimethylformamide and dimethyl sulphoxide, and also water.

Suitable Solid Carriers Are:

for example ammonium salts and ground natural minerals such as kaolins, clays, talc, chalk, quartz, attapulgite, montmorillonite or diatomaceous earth, and ground synthetic minerals, such as highly disperse silica, alumina and silicates; suitable solid carriers for granules are: for example crushed and fractionated natural rocks such as calcite, marble, pumice, sepiolite and dolomite, and also synthetic granules of inorganic and organic meals, and granules of organic material such as sawdust, coconut shells, maize cobs and tobacco stalks; suitable emulsifiers and/or foam-formers are: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and also protein hydrolysates; suitable dispersants are: for example lignosulphite waste liquors and methylcellulose.

Tackifiers such as carboxymethylcellulose and natural and synthetic polymers in the form of powders, granules or latices, such as gum arabic, polyvinyl alcohol and polyvinyl acetate, as well as natural phospholipids such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations generally comprise between 0.1 and 95% by weight of active compound, preferably between 0.5 and 90%.

The active compounds according to the invention can be used as such or in their formulations, including mixtures with known fungicides, bactericides, acaricides, nematicides or insecticides, so as, for example, to broaden the spectrum of action or prevent resistances developing. In many cases here, synergistic effects are obtained, i.e. the activity of the mixture is greater than the activity of the individual components.

Suitable co-components are, for example, the following compounds:

Fungicides:
aldimorph, ampropylfos, ampropylfos-potassium, andoprim, anilazine, azaconazole, azoxystrobin,
benalaxyl, benodanil, benomyl, benzamacril, benzamacryl-isobutyl, bialaphos, binapacryl, biphenyl, bitertanol, blasticidin-S, bromuconazole, bupirimate, buthiobate,
calcium polysulphide, capsimycin, captafol, captan, carbendazim, carboxin, carvon, quinomethionate, chlobenthiazone, chlorfenazole, chloroneb, chloropicrin, chlorothalonil, chlozolinate, clozylacon, cufraneb, cymoxanil, cyproconazole, cyprodinil, cyprofuram,
debacarb, dichlorophen, diclobutrazole, diclofluanid, diclomezine, dicloran, diethofencarb, difenoconazole, dimethirimol, dimethomorph, diniconazole, diniconazole-M, dinocap, diphenylamine, dipyrithione, ditalimfos, dithianon, dodemorph, dodine, drazoxolon,
edifenphos, epoxiconazole, etaconazole, ethirimol, etridiazole,
famoxadon, fenapanil, fenarimol, fenbuconazole, fenfuram, fenitropan, fenpiclonil, fenpropidin, fenpropimorph, fentin acetate, fentin hydroxide, ferbam, ferinizone, fluazinam, flumetover, fluoromide, fluquinconazole, flurprimidol, flusilazole, flusulfamide, flutolanil, flutriafol, folpet, fosetyl-aluminium, fosetyl-sodium, fthalide, fuberidazole, furalaxyl, furametpyr, furcarbonil, furconazole, furconazole-cis, fumnecyclox,
guazatine,
hexachlorobenzene, hexaconazole, hymexazole,
imazalil, imibenconazole, iminoctadine, iminoctadine albesilate, iminoctadine triacetate, iodocarb, ipconazole, iprobenfos (IBP), iprodione, irumnamycin, isoprothiolane, isovaledione,
kasugamycin, kresoxim-methyl, copper preparations, such as: copper hydroxide, copper naphthenate, copper oxychloride, copper sulphate, copper oxide, oxine-copper and Bordeaux mixture,
mancopper, mancozeb, maneb, meferimzone, mepanipyrim, mepronil, metalaxyl, metconazole, methasulfocarb, methfuroxam, metiram, metomeclam, metsulfovax, mildiomycin, myclobutanil, myclozolin,
nickel dimethyldithiocarbamate, nitrothal-isopropyl, nuarimol,
ofurace, oxadixyl, oxamocarb, oxolinic acid, oxycarboxim, oxyfenthiin,
paclobutrazole, pefurazoate, penconazole, pencycuron, phosdiphen, picoxystrobin, pimaricin, piperalin, polyoxin, polyoxorim, probenazole, prochloraz, procymidone, propamocarb, propanosine-sodium, propiconazole, propineb, pyraclostrobin, pyrazophos, pyrifenox, pyrimethanil, pyroquilon, pyroxyfur,
quinconazole, quintozene (PCNB),
sulphur and sulphur preparations,
tebuconazole, tecloftalam, tecnazene, tetcyclacis, tetraconazole, thiabendazole, thicyofen, thifluzamide, thiophanate-methyl, thiram, tioxymid, tolclofos-methyl, tolylfluanid, triadirnefon, triadirnenol, triazbutil, triazoxide, trichlamide, tricyclazole, tridemorph, trifloxystrobin, triflumizole, triforine, triticonazole,
uniconazole,
validamycin A, vinclozolin, viniconazole,
zarilamide, zineb, ziram and also Dagger G,
OK-8705,
OK-8801,
α-(1,1-dimethylethyl)-β-(2-phenoxyethyl)-1H-1,2,4-triazole-1-ethanol,
α-(2,4-dichlorophenyl)-β-fluoro-β-propyl-1H-1,2,4-triazole-1-ethanol,
α-(2,4-dichlorophenyl)-β-methoxy-β-methyl-1H-1,2,4-triazole-1-ethanol,
α-(5-methyl-1,3-dioxan-5-yl)-β-[[4-(trifluoromethyl)-phenyl]-methylene]-1H-1,2,4-triazole-1-ethanol,
(5RS,6RS)-6-hydroxy-2,2,7,7-tetramethyl-5-(1H-1,2,4-triazol-1-yl)-3-octanone,
(E)-α-(methoxyimino)-N-methyl-2-phenoxy-phenylacetamide,
1-isopropyl{2-methyl-1-[[[1-(4-methylphenyl)ethyl]amino]carbonyl]propyl}carbamate,
1-(2,4-dichlorophenyl)-2-(1H-1,2,4-triazol-1-yl)-ethanone-O-(phenylmethyl)-oxime,
1-(2-methyl-1-naphthalenyl)-1H-pyrrole-2,5-dione,
1-(3,5-dichlorophenyl)-3-(2-propenyl)-2,5-pyrrolidinedione,
1-[(diiodomethyl)-sulphonyl]-4-methyl-benzene,
1-[[2-(2,4-dichlorophenyl)-1,3-dioxolan-2-yl]-methyl]-1H-imidazole,
1-[[2-(4-chlorophenyl)-3-phenyloxiranyl]-methyl]-1H-1,2,4-triazole,
1-[1-[2-[(2,4-dichlorophenyl)-methoxy]-phenyl]-ethenyl]-1H-imidazole,
1-methy-5-nonyl-2-(phenylmethyl)-3-pyrrolidinole,
2',6'-dibromo-2-methyl-4'-trifluoromethoxy-4'-trifluoromethyl-1,3-thiazole-5-carboxanilide,
2,2-dichloro-N-[1-(4-chlorophenyl)-ethyl]-1-ethyl-3-methylcyclopropanecarboxamide,
2,6-dichloro-5-(methylthio)-4-pyrimidinyl-thiocyanate,
2,6-dichloro-N-(4-trifluoromethylbenzyl)-benzamide,
2,6-dichloro-N-[[4-(trifluoromethyl)-phenyl]-methyl]-benzamide,
2-(2,3,3-triiodo-2-propenyl)-2H-tetrazole, 2-[(1-methyl-ethyl)-sulphonyl]-5-(trichloromethyl)-1,3,4-thiadiazole,
2-[[6-deoxy-4-O-(4-O-methyl-β-D-glycopyranosyl)-α-D-glucopyranosyl]-amino]-4-methoxy-1-pyrrolo[2,3-d]pyrimidine-5-carbonitrile,
2-aminobutane,
2-bromo-2-(bromomethyl)-pentanedinitrile,
2-chloro-N-(2,3-dihydro-1,1,3-trimethyl-1H-inden-4-yl)-3-pyridinecarboxamide,
2-chloro-N-(2,6-dimethylphenyl)-N-(isothocyanatomethyl)-acetamide,
2-phenylphenol (OPP),
3,4-dichloro-1-[4-(difluoromethoxy)-phenyl]-1H-pyrrole-2,5-dione,
3,5-dichloro-N-[cyano[(1-methyl-2-propynyl)-oxy]-methyl]-benzamide,
3-(1,1-dimethylpropyl)-1-oxo-1H-indene-2-carbonitrile,
3-[2-(4-chlorophenyl)-5-ethoxy-3-isoxazolidinyl]-pyridine,
4-chloro-2-cyano-N,N-dimethyl-5-(4-methylphenyl)-1H-imidazole-1-sulphonamide,
4-methyl-tetrazolo[1,5-a]quinazolin-5(4H)-one,
8-(1,1-dimethylethyl)-N-ethyl-N-propyl-1,4-dioxaspiro[4.5]decane-2-methanamine,
8-hydroxyquinoline sulphate,
9H-xanthene-2-[(phenylamino)-carbonyl]-9-carboxylic hydrazide,
bis-(1-methylethyl)-3-methyl-4-[(3-methylbenzoyl)-oxy]-2,5-thiophenedicarboxylate, cis-1-(4-chlorophenyl)-2-(1H-1,2,4-triazol-1-yl)-cycloheptanol,
cis-4-[3-[4(1,1-dimethylpropyl)-phenyl]-2-methylpropyl]-2,6-dimethyl-morpholine hydrochloride,
ethyl [(4-chlorophenyl)-azo]-cyanoacetate,
potassium bicarbonate,
methanetetrathiol-sodium salt,
methyl 1-(2,3-dihydro-2,2-dimethyl-1H-inden-1-yl)-1H-imidazole-5-carboxylate,
methyl N-(2,6-dimethylphenyl)-N-(5-isoxazolylcarbonyl)-DL-alaninate,
methyl N-(chloroacetyl)-N-(2,6-dimethylphenyl)-DL-alaninate,
N-(2,3-dichloro-4-hydroxyphenyl)-1-methylcyclohexanecarboxamide,
N-(2,6-dimethylphenyl)-2-methoxy-N-(tetrahydro-2-oxo-3-furanyl)-acetamide,
N-(2,6-dimethylphenyl)-2-methoxy-N-(tetrahydro-2-oxo-3-thienyl)-acetamide,
N-(2-chloro-4-nitrophenyl)-4-methyl-3-nitro-benzenesulphonamide,
N-(4-cyclohexylphenyl)-1,4,5,6-tetrahydro-2-pyrimidineamine,
N-(4-hexylphenyl)-1,4,5,6-tetrahydro-2-pyrimidineamine,
N-(5-chloro-2-methylphenyl)-2-methoxy-N-(2-oxo-3-oxazolidinyl)-acetamide,
N-(6-methoxy-3-pyridinyl)-cyclopropanecarboxamide,
N-[2,2,2-trichloro-1-[(chloroacetyl)-amino]-ethyl]-benzamide,
N-[3-chloro-4,5-bis-(2-propinyloxy)-phenyl]-N'-methoxy-methaneimidamide,
N-formyl-N-hydroxy-DL-alanine-sodium salt,
O,O-diethyl [2-(dipropylamino)-2-oxoethyl]-ethylphosphoramidothioate,
O-methyl S-phenyl phenylpropylphosphoramidothioate,
S-methyl 1,2,3-benzothiadiazole-7-carbothioate,
spiro[2H]-1-benzopyran-2,1'(3'H)-isobenzofuran-3'-one,
4-[3,4-dimethoxyphenyl-3-(4-fluorophenyl)-acryloyl]-morpholine.

Bactericides:
bronopol, dichlorophen, nitrapyrin, nickel dimethyldithiocarbamate, kasugamycin, octhiinone, furancarboxylic acid, oxytetracyclin, probenazole, streptomycin, tecloftalam, copper sulphate and other copper preparations.

Insecticides/Acaricides/Nematicides:
abamectin, acephate, acetamiprid, acrinathrin, alanycarb, aldicarb, aldoxycarb, alphacypermethrin, alphamethrin, amitraz, avermectin, AZ 60541, azadirachtin, azamethiphos, azinphos A, azinphos M, azocyclotin,
*Bacillus popilliae, Bacillus sphaericus, Bacillus subtilis, Bacillus thuringiensis*, baculoviruses, *Beauveria bassiana, Beauveria tenella*, bendiocarb, benfuracarb, bensultap, benzoximate, betacyfluthrin, bifenazate, bifenthrin, bioethanomethrin, biopermethrin, bistrifluron, BPMC, bromophos A, bufencarb, buprofezin, butathiofos, butocarboxim, butylpyridaben,
cadusafos, carbaryl, carbofuran, carbophenothion, carbosulfan, cartap, chloethocarb, chlorethoxyfos, chlorfenapyr, chlorfenvinphos, chlorfluazuron, chlormephos, chlorpyrifos, chlorpyrifos M, chlovaporthrin, chromafenozide, cis-resmethrin, cispermethrin, clocythrin, cloethocarb, clofentezine, clothianidine, cyanophos, cyprene, cycloprothrin, cyfluthrin, cyhalothrin, cyhexatin, cypermethrin, cyromazine,
deltamethrin, demeton M, demeton S, demeton-S-methyl, diafenthiuron, diazinon, dichlorvos, dicofol, diflubenzuron, dimethoate, dimethylvinphos, diofenolan, disulfoton, docusat-sodium, dofenapyn,
eflusilanate, emamectin, empenthrin, endosulfan, *Entomopfthora* spp., esfenvalerate, ethiofencarb, ethion, ethoprophos, etofenprox, etoxazole, etrimfos,
fenamiphos, fenazaquin, fenbutatin oxide, fenitrothion, fenothiocarb, fenoxacrim, fenoxycarb, fenpropathrin, fenpyrad, fenpyrithrin, fenpyroximate, fenvalerate, fipronil, fluazinam, fluazuron, flubrocythrinate, flucycloxuron, flucythrinate, flufenoxuron, flumethrin, flutenzine, fluvalinate, fonophos, fosmethilan, fosthiazate, fubfenprox, furathiocarb,
granulosis viruses,
halofenozide, HCH, heptenophos, hexaflumuron, hexythiazox, hydroprene,
imidacloprid, indoxacarb, isazofos, isofenphos, isoxathion, ivermectin,
nuclear polyhedrosis viruses,
lambda-cyhalothrin, lufenuron,
malathion, mecarbam, metaldehyde, methamidophos, *Metharhizium anisopliae, Metharhizium flavoviride*, methidathion, methiocarb, methoprene, methomyl, methoxyfenozide, metolcarb, metoxadiazone, mevinphos, milbemectin, milbemycin, monocrotophos,
naled, nitenpyram, nithiazine, novaluron,
omethoate, oxamyl, oxydemethon M,
*Paecilomyces fumosoroseus*, parathion A, parathion M, permethrin, phenthoate, phorate, phosalone, phosmet, phosphamidon, phoxim, pirimicarb, pirimiphos A, pirimiphos M, profenofos, promecarb, propargite, propoxur, prothiofos, prothoate, pymetrozine, pyraclofos, pyresmethrin, pyrethrum, pyridaben, pyridathion, pyrimidifen, pyriproxyfen,
quinalphos,
ribavirin,
salithion, sebufos, silafluofen, spinosad, spirodiclofen, sulfotep, sulprofos,
tau-fluvalinate, tebufenozide, tebufenpyrad, tebupirimiphos, teflubenzuron, tefluthrin, temephos, temivinphos, terbufos, tetrachlorvinphos, tetradifon, thetacypermethrin, thiacloprid, thiamethoxam, thiapronil, thiatriphos, thiocyclam hydrogen oxalate, thiodicarb, thiofanox, thuringiensin, tralocythrin, tralomethrin, triarathene, triazamate, triazophos, triazuron, trichlophenidine, trichlorfon, triflumuron, trimethacarb,
vamidothion, vaniliprole, *Verticillium lecanii*,
YI 5302,
zeta-cypermethrin, zolaprofos,
(1R-cis)-[5-(phenylmethyl)-3-furanyl]-methyl 3-[(dihydro-2-oxo-3(2H)-furanylidene)-methyl]-2,2-dimethylcyclopropanecarboxylate,
(3-phenoxyphenyl)-methyl 2,2,3,3-tetramethylcyclopropanecarboxylate,
1-[(2-chloro-5-thiazolyl)methyl]tetrahydro-3,5-dimethyl-N-nitro-1,3,5-triazine-2(1H)-imine,
2-(2-chloro-6-fluorophenyl)-4-[4-(1,1-dimethylethyl)phenyl]-4,5-dihydro-oxazole,
2-(acetyloxy)-3-dodecyl-1,4-naphthalenedione,
2-chloro-N-[[[4-(1-phenylethoxy)-phenyl]-amino]-carbonyl]-benzamide,
2-chloro-N-[[[4-(2,2-dichloro-1,1-difluoroethoxy)-phenyl]-amino]-carbonyl]-benzamide,
3-methylphenyl propylcarbamate,
4-[4-(4-ethoxyphenyl)-4-methylpentyl]-1-fluoro-2-phenoxy-benzene, 4-chloro-2-(1,1-dimethylethyl)-5-[[2-(2,6-dimethyl-4-phenoxyphenoxy)ethyl]thio]-3(2H)-pyridazinone,
4-chloro-2-(2-chloro-2-methylpropyl)-5-[(6-iodo-3-pyridinyl)methoxy]-3(2H)-pyridazinone,
4-chloro-5-[(6-chloro-3-pyridinyl)methoxy]-2-(3,4-dichlorophenyl)-3(2H)-pyridazinone,
*Bacillus thuringiensis* strain EG-2348,
2-benzoyl-1-(1,1-dimethylethyl)-hydrazinobenzoic acid,
2,2-dimethyl-3-(2,4-dichlorophenyl)-2-oxo-1-oxaspiro[4.5]dec-3-en-4-yl butanoate,
[3-[(6-chloro-3-pyridinyl)methyl]-2-thiazolidinylidene]-cyanamide,
dihydro-2-(nitromethylene)-2H-1,3-thiazine-3(4H)-carboxaldehyde,
ethyl[2-[[1,6-dihydro-6-oxo-1-(phenyhnethyl)-4-pyridazinyl]oxy]ethyl]-carbamate,
N-(3,4,4-trifluoro-1-oxo-3-butenyl)-glycine,
N-(4-chlorophenyl)-3-[4-(difluoromethoxy)phenyl]-4,5-dihydro-4-phenyl-1H-pyrazole-1-carboxamide,
N-[(2-chloro-5-thiazolyl)methyl]-N'-methyl-N"-nitroguanidine,
N-methyl-N'-(1-methyl-2-propenyl)-1,2-hydrazinedicarbothioamide,
N-methyl-N'-2-propenyl-1,2-hydrazinedicarbothioamide,
O,O-diethyl[2-(dipropylamino)-2-oxoethyl]-ethylphosphoramidothioate,
N-cyanomethyl-4-trifluoromethyl-nicotinamide,
3,5-dichloro-1-(3,3-dichloro-2-propenyloxy)-4-[3-(5-trifluoromethylpyridin-2-yloxy)-propoxy]-benzene.

It is also possible to admix other known active compounds, such as herbicides, fertilizers and growth regulators.

When used as insecticides, the active compounds according to the invention can furthermore be present in their commercially available formulations and in the use forms, prepared from these formulations, in a mixture with synergistic agents. Synergistic agents are compounds which increase the action of the active compounds, without it being necessary for the synergistic agent added to be active itself.

The active compound content of the use forms prepared from the commercially available formulations can vary within wide limits. The active compound concentration of the use forms can be from 0.0000001 to 95% by weight of active compound, preferably between 0.0001 and 1% by weight.

The compounds are employed in a customary manner appropriate for the use forms.

When used against hygiene pests and pests of stored products, the active compound is distinguished by an excellent residual action on wood and clay as well as a good stability to alkali on limed substrates.

As already mentioned above, it is possible to treat all plants and their parts according to the invention. In a preferred embodiment, wild plant species and plant cultivars, or those obtained by conventional biological breeding methods, such as crossing or protoplast fusion, and parts thereof, are treated. In a further preferred embodiment, transgenic plants and plant cultivars obtained by genetic engineering, if appropriate in combination with conventional methods (Genetically Modified Organisms), and parts thereof are treated. The term "parts" or "parts of plants" or "plant parts" has been explained above.

Particularly preferably, plants of the plant cultivars which are in each case commercially available or in use are treated according to the invention. Plant cultivars are to be understood as meaning plants having new properties ("traits") which have been obtained by conventional breeding, by mutagenesis or by recombinant DNA techniques. These can be varieties, bio- and genotypes.

Depending on the plant species or plant cultivars, their location and growth conditions (soils, climate, vegetation period, diet), the treatment according to the invention may also result in superadditive ("synergistic") effects. Thus, for example, reduced application rates and/or a widening of the activity spectrum and/or an increase in the activity of the substances and compositions to be used according to the invention, better plant growth, increased tolerance to high or low temperatures, increased tolerance to drought or to water or soil salt content, increased flowering performance, easier harvesting, accelerated maturation, higher harvest yields, better quality and/or a higher nutritional value of the harvested products, better storage stability and/or processability of the harvested products are possible which extend beyond the effects which were actually to be expected.

The preferred transgenic plants or plant cultivars (i.e. those obtained by genetic engineering) which are to be treated according to the invention include all plants which, in the genetic modification, received genetic material which imparted particular advantageous useful properties ("traits") to these plants. Examples of such properties are better plant growth, increased tolerance to high or low temperatures, increased tolerance to drought or to water or soil salt content, increased flowering performance, easier harvesting, accelerated maturation, higher harvest yields, better quality and/or a higher nutritional value of the harvested products, better storage stability and/or processability of the harvested products. Further and particularly emphasized examples of such properties are a better defence of the plants against animal and microbial pests, such as against insects, mites, phytopathogenic fungi, bacteria and/or viruses, and also increased tolerance of the plants to certain herbicidally active compounds. Examples of transgenic plants which may be mentioned are the important crop plants, such as cereals (wheat, rice), maize, soya beans, potatoes, cotton, oilseed rape and also fruit plants (with the fruits apples, pears, citrus fruits and grapevines), and particular emphasis is given to maize, soya beans, potatoes, cotton and oilseed rape. Traits that are emphasized are in particular increased defence of the plants against insects by toxins formed in the plants, in particular those formed in the plants by the genetic material from *Bacillus thuringiensis* (for example by the genes CryIA(a), CryIA(b), CryIA(c), CryIIA, CryIIIA, CryIIIB2, Cry9c, Cry2Ab, Cry3Bb and CryIF and also combinations thereof) (hereinbelow referred to as "Bt plants"). Traits that are also particularly emphasized are the increased defence of plants against fungi, bacteria and viruses by systemic acquired resistance (SAR), systemin, phytoalexins, elicitors and resistance genes and correspondingly expressed proteins and toxins. Traits that are furthermore particularly emphasized are the increased tolerance of the plants to certain herbicidally active compounds, for example imidazolinones, sulphonylureas, glyphosate or phosphinotricin (for example the "PAT" gene). The genes which impart the desired traits in question can also be present in combinations with one another in the transgenic plants. Examples of "Bt plants" which may be mentioned are maize varieties, cotton varieties, soya bean varieties and potato varieties which are sold under the trade names YIELD GARD® (for example maize, cotton, soya beans), KnockOut® (for example maize), StarLink® (for example maize), Bollgard® (cotton), Nucotn® (cotton) and NewLeaf® (potato). Examples of herbicide-tolerant plants which may be mentioned are maize varieties, cotton varieties and soya bean varieties which are sold under the trade names Roundup Ready® (tolerance to glyphosate, for example maize, cotton, soya bean), Liberty Link® (tolerance to phosphinotricin, for example oilseed rape), IMI® (tolerance to imidazolinones) and STS® (tolerance to sulphonylureas, for example maize). Herbicide-resistant plants (plants bred in a conventional manner for herbicide tolerance) which may be mentioned include the varieties sold under the name Clearfield® (for example maize). Of course, these statements also apply to plant cultivars having these or still to be developed genetic traits, which plants will be developed and/or marketed in the future.

The plants listed can be treated according to the invention in a particularly advantageous manner with the compounds of the general formula I or the active compound mixtures according to the invention. The preferred ranges stated above for the active compounds or mixtures also apply to the treatment of these plants. Particular emphasis is given to the treatment of plants with the compounds or the mixtures specifically mentioned in the present text.

The active compounds according to the invention act not only against plant, hygiene and stored product pests, but also in the veterinary medicine sector against animal parasites (ectoparasites), such as hard ticks, soft ticks, mange mites, leaf mites, flies (biting and licking), parasitic fly larvae, lice, hair lice, feather lice and fleas. These parasites include:

From the order of the Anoplurida, for example, *Haematopinus* spp., *Linognathus* spp., *Pediculus* spp., *Phtirus* spp. and *Solenopotes* spp.

From the order of the Mallophagida and the suborders Amblycerina and Ischnocerina, for example, *Trimenopon* spp., *Menopon* spp., *Trinoton* spp., *Bovicola* spp., *Wemeckiella* spp., *Lepikentron* spp., *Damalina* spp., *Trichodectes* spp. and *Felicola* spp.

From the order of the Diptera and the suborders Nematocerina and Brachycerina, for example, *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp. and *Melophagus* spp.

From the order of the Siphonapterida, for example, *Pulex* spp., *Ctenocephalides* spp., *Xenopsylla* spp. and *Ceratophyllus* spp.

From the order of the Heteropterida, for example, *Cimex* spp., *Triatoma* spp., *Rhodnius* spp. and *Panstrongylus* spp.

From the order of the Blattarida, for example, *Blatta orientalis, Periplaneta americana, Blattella germanica* and *Supella* spp.

From the subclass of the Acaria (Acarida) and the orders of the Meta- and Mesostigmata, for example, *Argas* spp., *Ornithodorus* spp., *Otobius* spp., *Ixodes* spp., *Amblyomma* spp., *Boophilus* spp., *Dermacentor* spp., *Haemophysalis* spp., *Hyalomma* spp., *Rhipicephalus* spp., *Dermanyssus* spp., *Raillietia* spp., *Pneumonyssus* spp., *Stemostoma* spp. and *Varroa* spp.

From the order of the Actinedida (Prostigmata) and Acaridida (Astigmata), for example, *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp. and *Laminosioptes* spp.

The active compounds of the formula (I) according to the invention are also suitable for controlling arthropods which infest agricultural productive livestock, such as, for example, cattle, sheep, goats, horses, pigs, donkeys, camels, buffalo, rabbits, chickens, turkeys, ducks, geese and bees, other pets, such as, for example, dogs, cats, caged birds and aquarium fish, and also so-called test animals, such as, for example, hamsters, guinea pigs, rats and mice. By controlling these arthropods, cases of death and reduction in productivity (for meat, milk, wool, hides, eggs, honey etc.) should be diminished, so that more economic and easier animal husbandry is possible by use of the active compounds according to the invention.

The active compounds according to the invention are used in the veterinary sector in a known manner by enteral administration in the form of, for example, tablets, capsules, potions, drenches, granules, pastes, boluses, the feed-through process and suppositories, by parenteral administration, such as, for example, by injections (intramuscular, subcutaneous, intravenous, intraperitoneal and the like), implants, by nasal administration, by dermal use in the form, for example, of dipping or bathing, spraying, pouring on and spotting on, washing and powdering, and also with the aid of moulded articles containing the active compound, such as collars, ear marks, tail marks, limb bands, halters, marking devices and the like.

When used for cattle, poultry, pets and the like, the active compounds of the formula (I) can be used as formulations (for example powders, emulsions, free-flowing compositions), which comprise the active compounds in an amount of 1 to 80% by weight, directly or after 100 to 10 000-fold dilution, or they can be used as a chemical bath.

It has furthermore been found that the compounds according to the invention have a strong insecticidal action against insects which destroy industrial materials.

The following insects may be mentioned as examples and as preferences—but without a limitation:

Beetles, such as

*Hylotrupes bajulus, Chlorophorus pilosis, Anobium punctatum, Xestobium rufovillosum, Ptilinus pecticornis, Dendrobium pertinex, Emobius mollis, Priobium carpini, Lyctus brunneus, Lyctus africanus, Lyctus planicollis, Lyctus linearis, Lyctus pubescens, Trogoxylon aequale, Minthes rugicollis, Xyleborus* spec., *Tryptodendron* spec., *Apate monachus, Bostrychus capucins, Heterobostrychus brunneus, Sinoxylon* spec. and *Dinoderus minutus.*

Hymenopterons, such as

*Sirex juvencus, Urocerus gigas, Urocerus gigas taignus* and *Urocerus augur.*

Termites, such as

*Kalotermes flavicollis, Cryptotermes brevis, Heterotermes indicola, Reticulitermes flavipes, Reticulitermes santonensis, Reticulitermes lucifugus, Mastotermes darwiniensis, Zootermopsis nevadensis* and *Coptotermes formosanus.*

Bristletails, such as *Lepisma saccharina.*

Industrial materials in the present connection are to be understood as meaning non-living materials, such as, preferably, plastics, adhesives, sizes, papers and cards, leather, wood and processed wood products and coating compositions.

Wood and processed wood products are materials to be protected, especially preferably, from insect infestation.

Wood and processed wood products which can be protected by the agent according to the invention or mixtures comprising it are to be understood as meaning, for example:

building timber, wooden beams, railway sleepers, bridge components, boat jetties, wooden vehicles, boxes, pallets, containers, telegraph poles, wood panelling, wooden window frames and doors, plywood, chipboard, joinery or wooden products which are used quite generally in house-building or in building joinery.

The active compounds can be used as such, in the form of concentrates or in generally customary formulations, such as powders, granules, solutions, suspensions, emulsions or pastes.

The formulations mentioned can be prepared in a manner known per se, for example by mixing the active compounds with at least one solvent or diluent, emulsifier, dispersing agent and/or binder or fixing agent, a water repellent, if appropriate siccatives and UV stabilizers and if appropriate dyestuffs and pigments, and also other processing auxiliaries.

The insecticidal compositions or concentrates used for the protection of wood and wood-derived timber products comprise the active compound according to the invention in a concentration of 0.0001 to 95% by weight, in particular 0.001 to 60% by weight.

The amount of the compositions or concentrates employed depends on the nature and occurrence of the insects and on the medium. The optimum amount employed can be determined for the use in each case by series of tests. In general, however, it is sufficient to employ 0.0001 to 20% by weight, preferably 0.001 to 10% by weight, of the active compound, based on the material to be protected.

Solvents and/or diluents which are used are an organic chemical solvent or solvent mixture and/or an oily or oil-like organic chemical solvent or solvent mixture of low volatility and/or a polar organic chemical solvent or solvent mixture and/or water, and if appropriate an emulsifier and/or wetting agent.

Organic chemical solvents which are preferably used are oily or oil-like solvents having an evaporation number above 35 and a flashpoint above 30° C., preferably above 45° C. Substances which are used as such oily or oil-like water-insoluble solvents of low volatility are appropriate mineral oils or aromatic fractions thereof, or solvent mixtures containing mineral oils, preferably white spirit, petroleum and/or alkylbenzene.

Mineral oils having a boiling range from 170 to 220° C., white spirit having a boiling range from 170 to 220° C., spindle oil having a boiling range from 250 to 350° C., petroleum and aromatics having a boiling range from 160 to 280° C., terpentine oil and the like, are advantageously employed.

In a preferred embodiment, liquid aliphatic hydrocarbons having a boiling range from 180 to 210° C. or high-boiling mixtures of aromatic and aliphatic hydrocarbons having a boiling range from 180 to 220° C. and/or spindle oil and/or monochloronaphthalene, preferably α-monochloronaphthalene, are used.

The organic oily or oil-like solvents of low volatility which have an evaporation number above 35 and a flashpoint above 30° C., preferably above 45° C., can be replaced in part by organic chemical solvents of high or medium volatility, provided that the solvent mixture likewise has an evaporation number above 35 and a flashpoint above 30° C., preferably above 45° C., and that the insecticide/fungicide mixture is soluble or emulsifiable in this solvent mixture.

According to a preferred embodiment, some of the organic chemical solvent or solvent mixture is replaced by an aliphatic polar organic chemical solvent or solvent mixture. Aliphatic organic chemical solvents containing hydroxyl and/or ester and/or ether groups, such as, for example, glycol ethers, esters or the like, are preferably used.

Organic chemical binders which are used in the context of the present invention are the synthetic resins and/or binding drying oils which are known per se, are water-dilutable and/or are soluble or dispersible or emulsifiable in the organic chemical solvents employed, in particular binders consisting of or comprising an acrylate resin, a vinyl resin, for example polyvinyl acetate, polyester resin, polycondensation or polyaddition resin, polyurethane resin, alkyd resin or modified alkyd resin, phenolic resin, hydrocarbon resin, such as indene-coumarone resin, silicone resin, drying vegetable oils and/or drying oils and/or physically drying binders based on a natural and/or synthetic resin.

The synthetic resin used as the binder can be employed in the form of an emulsion, dispersion or solution. Bitumen or bituminous substances can also be used as binders in an amount of up to 10% by weight. Dyestuffs, pigments, water-repelling agents, odour correctants and inhibitors or anticorrosive agents and the like which are known per se can additionally be employed.

It is preferred according to the invention for the composition or concentrate to comprise, as the organic chemical binder, at least one alkyd resin or modified alkyd resin and/or a drying vegetable oil. Alkyd resins having an oil content of more than 45% by weight, preferably 50 to 68% by weight, are preferably used according to the invention.

All or some of the binder mentioned can be replaced by a fixing agent (mixture) or a plasticizer (mixture). These additives are intended to prevent evaporation of the active compounds and crystallization or precipitation. They preferably replace 0.01 to 30% of the binder (based on 100% of the binder employed).

The plasticizers originate from the chemical classes of phthalic acid esters, such as dibutyl, dioctyl or benzyl butyl phthalate, phosphoric acid esters, such as tributyl phosphate, adipic acid esters, such as di-(2-ethylhexyl) adipate, stearates, such as butyl stearate or amyl stearate, oleates, such as butyl oleate, glycerol ethers or higher molecular weight glycol ethers, glycerol esters and p-toluenesulphonic acid esters.

Fixing agents are based chemically on polyvinyl alkyl ethers, such as, for example, polyvinyl methyl ether or ketones, such as benzophenone or ethylenebenzophenone.

Possible solvents or diluents are, in particular, also water, if appropriate as a mixture with one or more of the above-mentioned organic chemical solvents or diluents, emulsifiers and dispersing agents.

Particularly effective preservation of wood is achieved by impregnation processes on a large industrial scale, for example vacuum, double vacuum or pressure processes.

The ready-to-use compositions can also comprise other insecticides, if appropriate, and also one or more fungicides, if appropriate.

Possible additional mixing partners are, preferably, the insecticides and fungicides mentioned in WO 94/29 268. The compounds mentioned in this document are an explicit constituent of the present application.

Very particularly preferred mixing partners which may be mentioned are insecticides, such as chlorpyriphos, phoxim, silafluofin, alphamethrin, cyfluthrin, cypermethrin, deltamethrin, permethrin, imidacloprid, NI-25, flufenoxuron, hexaflumuron, transfluthrin, thiacloprid, methoxyfenozide and triflumuron, and also fungicides, such as epoxyconazole, hexaconazole, azaconazole, propiconazole, tebuconazole, cyproconazole, metconazole, imazalil, dichlorfluanid, tolylfluanid, 3-iodo-2-propinyl butylcarbamate, N-octyl-isothiazolin-3-one and 4,5-dichloro-N-octylisothiazolin-3-one.

The compounds according to the invention can at the same time be employed for protecting objects which come into contact with salt water or brackish water, in particular hulls, screens, nets, buildings, moorings and signalling systems, against fouling.

Fouling by sessile Oligochaeta, such as Serpulidae, and by shells and species from the Ledamorpha group (goose barnacles), such as various *Lepas* and *Scalpellum* species, or by species from the Balanomorpha group (acorn barnacles), such as *Balanus* or *Pollicipes* species, increases the frictional drag of ships and, as a consequence, leads to a marked increase in operation costs owing to higher energy consumption and additionally frequent residence in the dry dock.

Apart from fouling by algae, for example *Ectocarpus* sp. and *Ceramium* sp., fouling by sessile Entomostraka groups, which come under the generic term Cirripedia (cirriped crustaceans), is of particular importance.

Surprisingly, it has now been found that the compounds according to the invention, alone or in combination with other active compounds, have an outstanding antifouling action.

Using the compounds according to the invention, alone or in combination with other active compounds, allows the use of heavy metals such as, for example, in bis(trialkyltin) sulphides, tri-n-butyltin laurate, tri-n-butyltin chloride, copper(I) oxide, triethyltin chloride, tri-n-butyl(2-phenyl-4-chlorophenoxy)-tin, tributyltin oxide, molybdenum disulphide, antimony oxide, polymeric butyl titanate, phenyl-(bispyridine)-bismuth chloride, tri-n-butyltin fluoride, manganese ethylenebisthiocarbamate, zinc dimethyldithiocarbamate, zinc ethylenebisthiocarbamate, zinc salts and copper salts of 2-pyridinethiol 1-oxide, bisdimethyldithiocarbamoylzinc ethylene-bisthiocarbamate, zinc oxide, copper(I) ethylene-bisdithiocarbamate, copper thiocyanate, copper naphthenate and tributyltin halides to be dispensed with, or the concentration of these compounds to be substantially reduced.

If appropriate, the ready-to-use antifouling paints can additionally comprise other active compounds, preferably algicides, fungicides, herbicides, molluscicides, or other antifouling active compounds.

Preferably suitable components in combinations with the antifouling compositions according to the invention are:
algicides such as
2-tert-butylamino-4-cyclopropylamino-6-methylthio-1,3,5-triazine, dichlorophen, diuron, endothal, fentin acetate, isoproturon, methabenzthiazuron, oxyfluorfen, quinoclamine and terbutryn;
fungicides such as
benzo[b]thiophenecarboxylic acid cyclohexylamide S,S-dioxide, dichlofluanid, fluorfolpet, 3-iodo-2-propinyl butylcarbamate, tolylfluanid and azoles such as azaconazole, cyproconazole, epoxyconazole, hexaconazole, metconazole, propiconazole and tebuconazole;
molluscicides such as
fentin acetate, metaldehyde, methiocarb, niclosamid, thiodicarb and trimethacarb;
or conventional antifouling active compounds such as
4,5-dichloro-2-octyl-4-isothiazolin-3-one, diiodomethylparatryl sulphone, 2-(N,N-dimethylthiocarbamoylthio)-5-nitrothiazyl, potassium, copper, sodium and zinc salts of 2-pyridinethiol 1-oxide, pyridine-triphenylborane, tetrabutyldistannoxane, 2,3,5,6-tetrachloro-4-(methylsulphonyl)-pyridine, 2,4,5,6-tetrachloroisophthalonitrile, tetramethylthiuram disulphide and 2,4,6-trichlorophenylmaleimide.

The antifouling compositions used comprise the active compound according to the invention of the compounds according to the invention in a concentration of 0.001 to 50% by weight, in particular 0.01 to 20% by weight.

Moreover, the antifouling compositions according to the invention comprise the customary components such as, for example, those described in Ungerer, Chem. Ind. 1985, 37, 730-732 and Williams, Antifouling Marine Coatings, Noyes, Park Ridge, 1973.

Besides the algicidal, fungicidal, molluscicidal active compounds and insecticidal active compounds according to the invention, antifouling paints comprise, in particular, binders.

Examples of recognized binders are polyvinyl chloride in a solvent system, chlorinated rubber in a solvent system, acrylic resins in a solvent system, in particular in an aqueous system, vinyl chloride/vinyl acetate copolymer systems in the form of aqueous dispersions or in the form of organic solvent systems, butadiene/styrene/acrylonitrile rubbers, drying oils such as linseed oil, resin esters or modified hardened resins in combination with tar or bitumens, asphalt and epoxy compounds, small amounts of chlorine rubber, chlorinated polypropylene and vinyl resins.

If appropriate, paints also comprise inorganic pigments, organic pigments or colorants which are preferably insoluble in salt water. Paints may furthermore comprise materials such as colophonium to allow controlled release of the active compounds. Furthermore, the paints may comprise plasticizers, modifiers which affect the rheological properties and other conventional constituents. The compounds according to the invention or the abovementioned mixtures may also be incorporated into self-polishing antifouling systems.

The active compounds are also suitable for controlling animal pests, in particular insects, arachnids and mites, which are found in enclosed spaces such as, for example, dwellings, factory halls, offices, vehicle cabins and the like. They can be employed alone or in combination with other active compounds and auxiliaries in domestic insecticide products for controlling these pests. They are active against sensitive and resistant species and against all development stages. These pests include:

From the order of the Scorpionidea, for example, *Buthus occitanus.*

From the order of the Acarina, for example, *Argas persicus, Argas reflexus, Bryobia* spp., *Dermanyssus gallinae, Glyciphagus domesticus, Ornithodorus moubat, Rhipicephalus sanguineus, Trombicula alfreddugesi, Neutrombicula autumnalis, Dermatophagoides pteronissimus* and *Dermatophagoides forinae.*

From the order of the Araneae, for example, *Avicularidae* and *Araneidae.*

From the order of the Opiliones, for example, *Pseudoscorpiones chelifer, Pseudoscorpiones cheiridium* and *Opiliones phalangium.*

From the order of the Isopoda, for example, *Oniscus asellus* and *Porcellio scaber.*

From the order of the Diplopoda, for example, *Blaniulus guttulatus* and *Polydesmus* spp.

From the order of the Chilopoda, for example, *Geophilus* spp.

From the order of the Zygentoma, for example, *Ctenolepisma* spp., *Lepisma saccharina* and *Lepismodes inquilinus.*

From the order of the Blattaria, for example, *Blatta orientalies, Blattella germanica, Blattella asahinai, Leucophaea maderae, Panchlora* spp., *Parcoblatta* spp., *Periplaneta australasiae, Periplaneta americana, Periplaneta brunnea, Periplaneta fuliginosa* and *Supella longipalpa*.

From the order of the Saltatoria, for example, *Acheta domesticus*.

From the order of the Dermaptera, for example, *Forficula auricularia*.

From the order of the Isoptera, for example, *Kalotermes* spp. and *Reticulitermes* spp.

From the order of the Psocoptera, for example, *Lepinatus* spp. and *Liposcelis* spp.

From the order of the Coleptera, for example, *Anthrenus* spp., *Attagenus* spp., *Dermestes* spp., *Latheticus oryzae, Necrobia* spp., *Ptinus* spp., *Rhizopertha dominica, Sitophilus granarius, Sitophilus oryzae, Sitophilus zeamais* and *Stegobium paniceum*.

From the order of the Diptera, for example, *Aedes aegypti, Aedes albopictus, Aedes taeniorhynchus, Anopheles* spp., *Calliphora erythrocephala, Chrysozona pluvialis, Culex quinquefasciatus, Culex pipiens, Culex tarsalis, Drosophila* spp., *Fannia canicularis, Musca domestica, Phlebotomus* spp., *Sarcophaga camaria, Simulium* spp., *Stomoxys calcitrans* and *Tipula paludosa*.

From the order of the Lepidoptera, for example, *Achroia grisella, Galleria mellonella, Plodia interpunctella, Tinea cloacella, Tinea pellionella* and *Tineola* bisselliella.

From the order of the Siphonaptera, for example, *Ctenocephalides canis, Ctenocephalides felis, Pulex irritans, Tunga penetrans* and *Xenopsylla* cheopis.

From the order of the Hymenoptera, for example, *Camponotus herculeanus, Lasius fuliginosus, Lasius niger, Lasius umbratus, Monomorium pharaonis, Paravespula* spp. and *Tetramorium caespitum*.

From the order of the Anoplura, for example, *Pediculus humanus capitis, Pediculus humanus corporis* and *Phthirus pubis*.

From the order of the Heteroptera, for example, *Cimex hemipterus, Cimex lectularius, Rhodinus prolixus* and *Triatoma infestans*.

In the field of household insecticides, they are used alone or in combination with other suitable active compounds, such as phosphoric acid esters, carbamates, pyrethroids, growth regulators or active compounds from other known classes of insecticides.

They are used as aerosols, unpressurized spray products, for example pump and atomizer sprays, automatic misting systems, foggers, foams, gels, evaporator products with evaporator tablets made of cellulose or polymer, liquid evaporators, gel and membrane evaporators, propeller-driven evaporators, unpowered or passive evaporation systems, moth papers, moth bags and moth gels, as granules or dusts, in baits for spreading or in bait stations.

PREPARATION EXAMPLES

Example (I-1)

6.84 g (8.1 mmol) of a 22% strength aqueous solution of N-(6-chloropyridin-3-ylmethyl)ethylene-1,2-diamine was concentrated to about 3 g using a rotary evaporator, transferred into a 50 ml flask using 20 ml of MeOH and cooled to −40° C. Over a period of 3 min, a solution of 1 g (3.7 mmol) 2-nitropentachloro-1,3-butadiene in 10 ml of MeOH was then added dropwise to this mixture, which was subsequently stirred at −40° C. for 1 h and at room temperature for 1 h. The resulting precipitate was filtered off with suction, washed with water (3×10 ml) and diethyl ether (3×10 ml) and dried under reduced pressure. This gave 0.42 g (30%) of 2-chloro-5-[2-(2,3,3-trichloro-1-nitroallylidene) imidazolidin-1-ylmethyl]pyridine.

Example (I-1)

Alternative Preparation Method

At room temperature, 10 g (12 mmol) of a 22% strength aqueous solution of N-(6-chloropyridin-3-ylmethyl)ethylene-1,2-diamine were added to a suspension of 1.08 g (3 mmol) of 1-(4-methylphenylthio)-2-nitro-1,3,4,4-tetrachlorobuta-1,3-diene in 30 ml of methanol, and this mixture was stirred at room temperature for 1 day. The resulting 1,1-bis-(4-methylphenylthio)-2-nitro-3,4,4-trichlorobuta-1,3-diene precipitate was filtered off, washed with water and cold methanol (2×3 ml) and dried under reduced pressure. The yield was 0.27 g (20%). The combined filtrate was, at 0° C., neutralized with conc. HCl and, with stirring, mixed with 50 ml of water. The precipitate was filtered off with suction, washed with water and ether (3×5 ml) and recrystallized from methanol. This gave 0.13 g (15%) of 2-chloro-5-[2,3,3-trichloro-1-nitroallylidene)imidazolidin-1-ylmethyl]pyridine.

Example (I-2)

At room temperature, a solution of 0.35 g (4 mmol) of morpholine in 5 ml of MeOH was added dropwise to a suspension of 0.5 g (1.3 mmol) of 2-chloro-5-[2-(2,3,3-trichloro-1-nitroallylidene)imidazolidin-1-ylmethyl]pyridine (compound of Example (I-1)) in 20 ml of methanol (MeOH), and the resulting mixture was stirred at room temperature for 3 h and at 40-45° C. for 3 h. After cooling to 10° C., excess morpholine was neutralized using 5% HCl (to pH 6-7), 70 ml of water were then added with stirring and the resulting precipitate was filtered off with suction, washed thoroughly with water and dried initially on a glass frit and then under reduced pressure. This gave 0.34 g (60%) of 2-chloro-5-[2-(2-morpholinyl-3,3-dichloro-1-nitro-allylidene)imidazolidin-1-ylmethyl]pyridine.

If, after mixing with water, the product separated out as an oil, the water was decanted off and the oil was dissolved in 10 ml of MeOH and allowed to stand either in a fridge or in a steam cupboard. In most cases, the product precipitates from methanol as a solid within 1-2 days.

Example (I-3)

At 0° C., a solution of 0.08 g (1.5 mmol) of sodium methoxide in 5 ml of methanol was added to a suspension of 0.5 g (1.3 mmol) of 2-chloro-5-[2-(2,3,3-trichloro-1-nitroallylidene)imidazolidin-1-ylmethyl]pyridine (compound of Example (I-1)) and 0.17 g (1.4 mmol) of 4-methylthiophenol in 15 ml of methanol, and the mixture was stirred at room temperature for 2 h and at 35° C. for 10 h. After cooling to 50° C., 3 drops of conc. HCl were added. The reaction mixture was then taken up in 50 ml of ice-water. The resulting precipitate was filtered off with suction and washed with methanol (3×7 ml), petroleum ether (3×7 ml) and finally with water. This gave 0.31 g (50%) of 2-chloro-5-[2-(2-(p-tolylthio)-3,3-dichloro-1-nitroallylidene)imidazolidin-1-ylmethyl]pyridine.

The other compounds of the formula (I) listed in the table are obtained in an analogous manner.

TABLE (I)

$$\underset{Z}{\overset{Hal}{\diagdown}}C=\underset{NO_2}{\overset{Y}{C}}-\underset{X}{\overset{R^2}{C}}=N-\overset{R^1}{CH}-A$$

| Ex. No. | A | R¹ | R² X | Y | Z | Hal | m.p. °C. |
|---|---|---|---|---|---|---|---|
| I-1 | 6-chloropyridin-3-yl | H | CH₂—CH₂—NH | Cl | Cl | Cl | 174-175 |
| I-2 | 6-chloropyridin-3-yl | H | CH₂—CH₂—NH | morpholin-4-yl | Cl | Cl | 92-94 |
| I-3 | 6-chloropyridin-3-yl | H | CH₂—CH₂—NH | —S—C₆H₄—CH₃ (4-tolylthio) | Cl | Cl | 204-206 |
| I-4* | 6-chloropyridin-3-yl | H | CH₂—CH₂—NH | Cl | Cl | Br | 172-173 |
| I-5 | 2-chloro-1,3-thiazol-5-yl | H | CH₂—CH₂—NH | H | NO₂ | Cl | 150-152 |
| I-6 | 6-chloropyridin-3-yl | H | CH₂—CH₂—O | Cl | Cl | Cl | 156-158 |
| I-7* | 6-chloropyridin-3-yl | H | CH(C₂H₅)—CH₂—O | Cl | Cl | Cl | 119-121 |
| I-8 | 6-chloropyridin-3-yl | H | CH₂—CH₂—NH | 2,6-dimethylpiperidin-1-yl | Cl | Cl | 130 |
| I-9 | 6-chloropyridin-3-yl | H | CH₂—CH₂—NH | piperidin-1-yl | Cl | Cl | 86-88 |
| I-10 | 6-chloropyridin-3-yl | H | CH₂—CH₂—NH | pyrrolidin-1-yl | Cl | Cl | 80-82 |
| I-11 | 6-chloropyridin-3-yl | H | CH₂—CH₂—NH | thiomorpholin-4-yl | Cl | Cl | 99-101 |

TABLE-continued (I)

$$A-CH(R^1)-N(R^2)-C(X)=C(NO_2)-C(Y)=C(Z)(Hal)$$

| Ex. No. | A | R¹ | R² | X | Y | Z | Hal | m.p. °C. |
|---|---|---|---|---|---|---|---|---|
| I-12 | 2-Cl-5-pyridyl | H | CH₂—CH₂—NH | —N(CH₃)C(CH₃)₃ | Cl | Cl | 105-107 |
| I-13 | 2-Cl-5-pyridyl | H | CH₂—CH₂—NH | —N(CH₃)CH(CH₃)₂ | Cl | Cl | 80-82 |
| I-14 | 2-Cl-5-pyridyl | H | CH₂—CH₂—NH | azepan-1-yl | Cl | Cl | 134-135 |
| I-15 | 2-Cl-5-pyridyl | H | CH₂—CH₂—NH | 1,4-dioxa-8-azaspiro[4.5]dec-8-yl | Cl | Cl | 179-181 |
| I-16 | 2-Cl-5-thiazolyl | H | CH₂—CH₂—NH | Cl | Cl | Cl | 153-154 |
| I-17 | 2-Cl-5-thiazolyl | H | CH₂—CH₂—NH | azepan-1-yl | Cl | Cl | 38-39 |
| I-18 | 2-Cl-5-thiazolyl | H | CH₂—CH₂—NH | 1,4-dioxa-8-azaspiro[4.5]dec-8-yl | Cl | Cl | 150-151 |
| I-19 | 2-Cl-5-pyridyl | H | CH₂—CH₂—NH | azocan-1-yl | Cl | Cl | 93-95 |
| I-20 | 2-Cl-5-thiazolyl | H | CH₂—CH₂—NH | azocan-1-yl | Cl | Cl | 63-65 |
| I-21 | 2-Cl-5-thiazolyl | H | CH₂—CH₂—NH | morpholin-4-yl | Cl | Cl | 120-121 |

TABLE-continued $$\underset{\substack{\text{A—CH—N}\\\text{Z}\quad\text{Hal}}}{\overset{R^1\quad R^2}{\underset{Y}{\bigg|}}}\overset{X}{\underset{NO_2}{\bigg|}}$$ (I)

| Ex. No. | A | R[1] | R[2] X | Y | Z | Hal | m.p. ° C. |
|---|---|---|---|---|---|---|---|
| I-22 | 2-chloro-5-methyl-thiazole | H | CH$_2$—CH$_2$—CH$_2$—NH | Cl | Cl | Cl | 137-139 |
| I-23 | 2-chloro-5-methyl-pyridine | H | CH$_2$—CH$_2$—CH$_2$—NH | morpholine | Cl | Cl | 94-96 |
| I-24 | 2-chloro-5-methyl-pyridine | H | CH$_2$—CH$_2$—CH$_2$—NH | H | NO$_2$ | Cl | 52-54 |
| I-25 | 2-chloro-5-methyl-thiazole | H | CH$_2$—CH$_2$—NH | H | NO$_2$ | Cl | 150-152 |
| I-26 | 2-chloro-5-methyl-pyridine | H | CH$_2$—CH$_2$—NH | SCH$_3$ | Cl | Cl | 84-86 |
| I-27 | 2-chloro-5-methyl-thiazole | H | CH$_2$—CH$_2$—NH | SCH$_3$ | Cl | Cl | 111-113 |
| I-28 | 2-chloro-5-methyl-thiazole | H | CH$_2$—CH$_2$—NH | 4-(3-chlorophenyl)piperazin-1-yl | Cl | Cl | 124-126 |
| I-29 | 2-chloro-5-methyl-pyridine | H | CH$_2$—CH$_2$—NH | N(CH$_3$)—CH$_2$—phenyl | Cl | Cl | 136-137 |
| I-30 | 2-chloro-5-methyl-pyridine | H | CH$_2$—CH$_2$—NCH3 | Cl | Cl | Cl | 153-154 |
| I-31 | 2-chloro-5-methyl-pyridine | H | CH$_2$—CH$_2$—NH | N(CH$_3$)$_2$ | Cl | Cl | 44-45 |
| I-32 | 2-chloro-5-methyl-pyridine | H | CH$_2$—CH$_2$—NH | 4-benzylpiperazin-1-yl | Cl | Cl | 155-156 |

TABLE-continued (I)

$$A-CH(R^1)-N(R^2)-C(X)=C(NO_2)-C(Y)=C(Z)(Hal)$$

| Ex. No. | A | R¹ | R² | X | Y | Z | Hal | m.p. °C. |
|---|---|---|---|---|---|---|---|---|
| I-33 | 2-Cl-pyridin-5-yl | H | | CH₂—CH₂—NH | H₃C—O—(CH₂)₂—N(CH) | Cl | Cl | viscous oil |

*is present as a Z,E isomer mixture

Example (II-1)

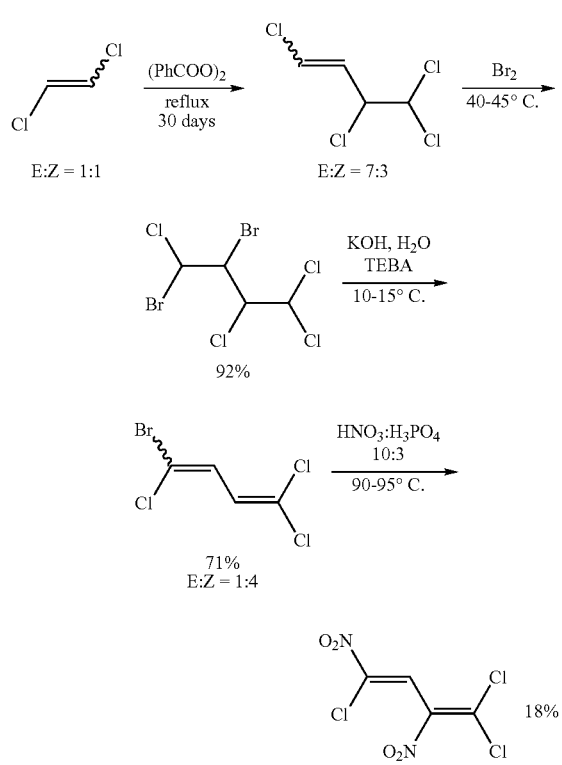

Z-1,3-Dinitro-1,4,4-trichloro-1,3-butadiene

1. Free-Radical Dimerization of 1,2-dichloroethylene 100 g of 75% strength water-containing benzoyl peroxide are dissolved in 0.5 l of 1,2-dichloroethylene (mixture of isomers, about 1:1, $d^{20}$=1.27 g/ml), and the organic phase is separated off, dried over CaCl₂ and finally transferred into a 2 l flask. A further 1.2 l of 1,2-dichloroethylene are added, as well as 3-5 boiling stones, and the mixture is heated under reflux for 30 d (about 10 h/d). (It is very important to add 3-4 fresh boiling stones to the flask every day to ensure uniform boiling of the mixture. It is recommended to monitor the evolution of CO₂ via a gas outlet at the reflux condenser). During the reaction, the boiling point of the reaction mixture increases by 10-15° C. When the reaction is ended, unreacted 1,2-dichloroethylene (about 1 l) is removed under water pump vacuum and the reaction mixture that remains is distilled under oil pump vacuum.

This gives about 1.25 kg ($d^{20}$=1.47 g/ml) of 1,3,4,4-tetrachloro-1-butene as Z:E isomer mixture of about 3:7 (b.p. 78-82° C./1 mm Hg), yield (based on converted 1,2-dichloroethylene) 70%.

2. Bromination of 1,3,4,4-tetrachloro-1-butene

At 40-45° C., 90 ml of bromine are added dropwise over a period of 3 h to 300 g of 1,3,4,4-tetrachloro-1-butene (magnetic stirrer, irradiation with a 100 W bulb), and the mixture is stirred at this temperature for another 8 h. When the reaction has ended (TLC), 100 ml of 5% strength Na₂S₂O₃ solution are added with stirring to the cooled reaction mixture, the mixture is stirred for 1 h and the organic phase (1,2-dibromo-1,3,4,4-tetrachlorobutane, about 500 g) is separated off, washed with water and used without additional purification for the dehydrohalogenation.

3. Dehydrohalogenation of 1,2-dibromo-1,3,4,4-tetrachlorbutane

At 10-15° C., a solution of 173 g of KOH and 20 g of TEBA in 300 ml of water is added dropwise with stirring over a period of 2 h to 500 g of 1,2-dibromo-1,3,4,4-tetrachlorobutane, stirring is continued at room temperature for another 6 h, the reaction mixture is neutralized with conc. HCl, the product is extracted with chloroform and dried over CaCl₂, the solvents are removed using a rotary evaporator and the mixture that remains is distilled under oil pump vacuum. This gives 237 g of 1-bromo-1,4,4-trichloro-1,3-butadiene (E:Z=1:4), yield 71%.

4. Nitration of 1-bromo-1,4,4-trichloro-1,3-butadiene

Nitrating acid is prepared from 400 ml of 65% strength $HNO_3$ and 120 ml of conc. $H_3PO_4$, introduced into a 1 l two-necked flask fitted with ground-joint stirrer, reflux condenser and dropping funnel and, with stirring, heated to 100-105° C. (the oil bath temperature must not exceed 115° C.). Over a period of 2 h, 230 g of 1-bromo-1,4,4-trichloro-1,3-butadiene are then added dropwise to the nitrating acid, and the resulting mixture is stirred at an oil bath temperature of 110-115° C. for another 1 h. After cooling to room temperature, the organic layer is separated off, the aqueous phase is extracted with petroleum ether (2×100 ml) and the combined organic phases are washed with water and dried using $CaCl_2$. The mixture is filtered through a paper filter and cooled with stirring to −10-15° C. and the resulting precipitate is filtered off with suction and washed with petroleum ether. This gives 43 g of Z-1,3-dinitro-1,4,4-trichloro-1,3-butadiene (m.p. 70-71° C.), yield 18%.

Example II-2

Z,E-4-Bromo-2-nitro-1,1,3,4-tetrachloro-1,3-butadiene

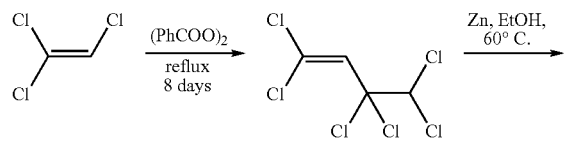

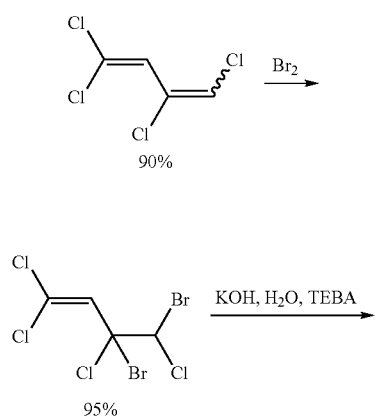

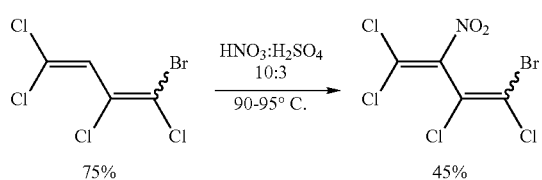

1. Free-Radical Dimerization of Trichloroethylene 100 g of 75% strength water-containing benzoyl peroxide are dissolved in 0.5 l of trichloroethylene ($d_4^{20}$=1.46 g/ml) and the organic phase is separated off in a separating funnel, dried over $CaCl_2$ and then transferred into a 2 l flask. A further 1.2 l of trichloroethylene and 3-4 boiling stones are added, and the mixture is heated under reflux for 12 d (about 10 h/d). (It is very important to add 3-4 fresh boiling stones to the flask every day to ensure uniform boiling of the mixture. It is recommended to monitor the evolution of $CO_2$ via a gas outlet at the reflux condenser). During the reaction, the boiling point of the reaction mixture increases from 86° C. (pure trichloroethylene) to 97-105° C. When the reaction is ended, unreacted trichloroethylene (about 1 l) is removed under water pump vacuum and the reaction mixture that remains is distilled under oil pump vacuum. This gives about 0.87 kg (about 0.52 l, $d^{20}$=1.67 g/ml) of 1,1,3,3,4,4-hexachloro-1-butene (b.p. 73-75° C./1 mm Hg), yield (based on converted trichloroethylene) 85%.

2. Dechlorination of 1,1,3,3,4,4-hexachloro-1-butene

Over a period of 2 h, 67 g of Zn powder are added to a solution of 263 g of 1,1,3,3,4,4-hexachloro-1-butene in 200 ml of ethanol such that the reaction temperature does not exceed 60° C., stirring is continued at 55-60° C. for another 5 h, the reaction mixture is cooled to room temperature, 500 ml of 1% strength HCl are added with stirring, the mixture is extracted with chloroform and the extract is dried with $CaCl_2$ and distilled under oil pump vacuum. This gives 173 g of Z,E-1,1,3,4-tetrachloro-1,3-butadiene (b.p. 68-69° C./1 mm Hg), yield 90%.

3. Bromination of 1,1,3,4-tetrachloro-1,3-butadiene

At 45-50° C., 26 ml of bromine are added dropwise over a period of 1 h to 96 g of 1,1,3,4-tetrachloro-1,3-butadiene (magnetic stirrer, irradiation with a 100 W bulb), and the mixture is stirred at this temperature for another 12 h. When the reaction has ended (TLC), 40 ml of 5% strength $Na_2S_2O_3$ solution are added with stirring to the cooled reaction mixture, the mixture is stirred for 1 h and the organic phase (3,4-dibromo-1,1,3,4-tetrachloro-1-butane, about 167 g) is separated off, washed with water and used without additional purification for the dehydrobromination.

4. Dehydrobromination of 3,4-dibromo-1,1,3,4-tetrachloro-1-butene

At 10-15° C., a solution of 5.8 g of KOH and 0.5 g of TEBA in 30 ml of water is added dropwise with stirring over a period of 1 h to 35.2 g of 3,4-dibromo-1,1,3,4-tetrachloro-1-butene, stirring is continued at room temperature for another 12 h and at 40-45° C. for 4 h, the reaction mixture is neutralized with conc. HCl, the product is extracted with chloroform and dried over $CaCl_2$, the solvents are removed using a rotary evaporator and the mixture that remains is distilled under oil pump vacuum. This gives 20.2 g of Z,E-1-bromo-1,2,4,4-trichloro-1,3-butadiene, yield 75%.

5. Nitration of 1-bromo-1,2,4,4-tetrachloro-1,3-butadiene

Nitrating acid is prepared from 200 ml of 65% strength $HNO_3$ and 65 ml of 98% strength $H_2SO_4$, introduced into a 0.5 l two-necked flask fitted with ground-joint stirrer, reflux condenser and dropping funnel and, with stirring, heated to 95-100° C. (the oil bath temperature must not exceed 110° C.). Over a period of 2 h, 136 g of Z,E-1-bromo-1,2,4,4-trichloro-1,3-butadiene are then added dropwise to the nitrating acid, and the resulting mixture is stirred at an oil bath temperature of 100-105° C. for another 3 h. After cooling to room temperature, the organic layer is separated off, the aqueous phase is extracted with chloroform the combined organic phases are washed with water, 5% strength $NaHCO_3$ solution and again water, dried using $CaCl_2$ and distilled under reduced pressure. Bromodichloroacrolein is distilled off as first fraction (about 4-8% of the total amount). The main fraction comprises 71 g of Z,E-4-bromo-2-nitro-1,1,3,4-tetrachloro-1,3-butadiene, yield 45%.

1-(4-Methylphenylthio)-2-nitro-1,3,4,4-tetrachlorobuta-1,3-diene

At room temperature, 4.72 g (38 mmol) of 4-methylthiophenol are added to a solution of 10.00 g (36.9 mmol) of 2-nitropentachloro-1,3-butadiene in 20 ml of ether, and the mixture is stirred for 20 h. The ether is then removed under reduced pressure, and the crystal slurry which is formed after addition of 20 ml of methanol is filtered off, washed with cold MeOH (2×10 ml) and dried under reduced pressure, yield 9.9 g (75%), $R_f$=0.72 ($Et_2O$: petroleum ether=1:3), m.p. 110-111° C.

1,1-Bis-(4-methylphenylthio)-2-nitro-3,4,4-trichlorobuta-1,3-diene

At 0° C., 5.05 g (75 mmol) of sodium ethoxide in 10 ml of ethanol are added dropwise over a period of 10 min to a solution of 10.00 g (36.9 mmol) of 2-nitropentachloro-1,3-butadiene and 9.3 g (75 mmol) of 4-methylthiophenol in 50 ml of ethanol. After 2 h of stirring at 0° C., the precipitate is separated off, washed with water and cold methanol (2×20 ml) and dried under reduced pressure, yield 14.5 g (88%), $R_f$=0.68 ($Et_2O$: petroleum ether=1:3), m.p. 117-118° C.

USE EXAMPLES

Example A

*Myzus* Test

| Solvent: | 7 parts by weight of dimethylformamide |
|---|---|
| Emulsifier: | 2 parts by weight of alkylaryl polyglycol ether |

To produce a suitable preparation of active compound, 1 part by weight of active compound is mixed with the stated amounts of solvent and emulsifier, and the concentrate is diluted with water to the desired concentration.

Broad bean seedlings (*Vicia faba minor*) which are infested by the green peach aphid (*Myzus persicae*) are dipped into a preparation of active compound of the desired concentration and placed into a plastic box.

After the desired period of time, the kill in % is determined. 100% means that all animals have been killed; 0% means that none of the animals have been killed.

In this test, for example, the following compounds of the Preparation Examples show good activity:

TABLE A

Plant-damaging insects

*Myzus* test

| Active compounds | Concentration of active compound in ppm | Kill rate in % after $6^d$ (days) |
|---|---|---|
| I-1 | 500 | 100 | according to the invention

| I-2 | 500 | 100 | according to the invention

Example B

Phaedon Larvae Test

| Solvent: | 3 parts by weight of dimethylformamide |
|---|---|
| Emulsifier: | 1 part by weight of alkylaryl polyglycol ether |

To produce a suitable preparation of active compound, 1 part by weight of active compound is mixed with the stated amounts of solvent and emulsifier, and the concentrate is diluted with emulsifier-containing water to the desired concentration.

Cabbage leaves (*Brassica oleracea*) are treated by being dipped into the preparation of active compound of the desired concentration and are populated with larvae of the mustard beetle (*Phaedon cochleariae*) while the leaves are still moist.

After the desired period of time, the kill in % is determined. 100% means that all beetle larvae have been killed; 0% means that none of the beetle larvae have been killed.

In this test, for example, the following compounds of the Preparation Examples show good activity:

TABLE B

Plant-damaging insects
*Phaedon* larvae test

| Active compounds | Concentration of active compound in ppm | Kill rate in % after 6$^d$ (days) |
|---|---|---|
| I-2 | 100 | 100 | according to the invention

Example C

*Plutella* Test

| Solvent: | 100 parts by weight of acetone |
| | 1 900 parts by weight of methanol |

To produce a suitable preparation of active compound, 1 part by weight of active compound is mixed with the stated amount of solvent and the concentrate is diluted with methanol to the desired concentrations.

The stated amount of the preparation of active compound of the desired concentration is pipetted onto a standardized amount of synthetic feed. After the methanol has evaporated, about 200-300 eggs of the diamondback moth (*Plutella xylostella*) are placed onto the feed.

After the desired period of time, the kill of the eggs and/or larvae in % is determined. 100% means that all animals have been killed; 0% means that none of the animals have been killed.

In this test, for example, the activity of the following compounds of the Preparation Examples is superior to compounds of the prior art:

TABLE C

Plant-damaging insects
*Plutella* test

| Active compounds | Concentration of active compound in ppm | Kill rate in % after 7$^d$ (days) |
|---|---|---|
| I-2 | 150 | 100 | according to the invention

Example D

*Aphis gossypii* Test

| Solvent: | 7 parts by weight of dimethylformamide |
| Emulsifier: | 2 parts by weight of alkylaryl polyglycol ether |

To produce a suitable preparation of active compound, 1 part by weight of active compound is mixed with the stated amounts of solvent and emulsifier, and the concentrate is diluted with emulsifier-containing water to the desired concentration.

Cotton leaves (*Gossypium hirsutum*) which are heavily infested by the cotton aphid (*Aphis gossypii*) are treated by being dipped into the preparation of active compound of the desired concentration.

After the desired period of time, the kill in % is determined. 100% means that all aphids have been killed; 0% means that none of the aphids have been killed.

In this test, for example, the following compounds of the Preparation Examples show good activity:

TABLE D

Plant-damaging insects

*Aphis gossypii* test

| Active compounds | Concentration of active compound in ppm | Kill rate in % after 6$^d$ (days) |
|---|---|---|
| I-2 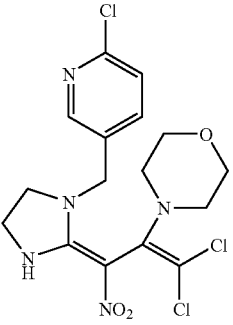 according to the invention | 500 | 100 |

Example E

Critical Concentration Test/Root-Systemic Action

| Test insect: | *Aphis gossypii* |
|---|---|
| Solvent: | 3.5 parts by weight of acetone |
| Emulsifier: | 1 part by weight of alkylaryl polyglycol ether |

To produce a suitable preparation of active compound, 1 part by weight of active compound is mixed with the stated amount of solvent, the stated amount of emulsifier is added and the concentrate is diluted with water to the desired concentration.

The preparation of active compound is poured onto the soil of the infected savoy cabbage plant. In this way, the active compound can be taken up from the soil by the roots of the plants and can be transported into the leaves. Here, the concentration of active compound in the preparation is virtually immaterial, only the amount by weight per volume unit of soil, which is stated in ppm (mg/ml), matters.

To demonstrate the root-systemic effect, evaluation is carried out after 10 days by counting or estimating the number of dead animals. The root-systemic action of the active compound is derived from the kill rate. It is 100% if all test animals have been killed and 0% if the number of test insects alive is the same as that for the untreated control.

Active compounds, application rates and results are shown in the table below:

TABLE E

Critical concentration test/root-systemic action

*Aphis gossypii*

| Active compounds | Concentration of active compound in ppm | Kill rate in % after 10$^d$ (days) |
|---|---|---|
| I-1 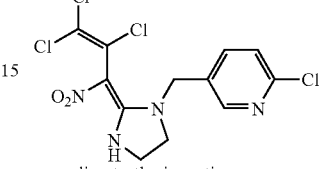 according to the invention | 20 | 100 |
| I-2 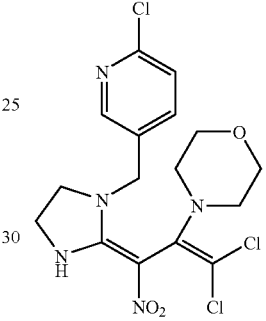 according to the invention | 20 | 100 |

Example F

Critical Concentration Test/Root-Systemic Action

| Test insect: | *Myzus persicae* |
|---|---|
| Solvent: | 3.5 parts by weight of acetone |
| Emulsifier: | 1 part by weight of alkylaryl polyglycol ether |

To produce a suitable preparation of active compound, 1 part by weight of active compound is mixed with the stated amount of solvent, the stated amount of emulsifier is added and the concentrate is diluted with water to the desired concentration.

The preparation of active compound is poured onto the soil of the infected savoy cabbage plant. In this way, the active compound can be taken up from the soil by the roots of the plants and can be transported into the leaves. Here, the concentration of active compound in the preparation is virtually immaterial, only the amount by weight per volume unit of soil, which is stated in ppm (mg/ml), matters.

To demonstrate the root-systemic effect, evaluation is carried out after 10 days by counting or estimating the number of dead animals. The root-systemic action of the active compound is derived from the kill rate. It is 100% if all test animals have been killed and 0% if the number of test insects alive is the same as that for the untreated control.

Active compounds, application rates and results are shown in the table below:

TABLE F

Critical concentration test/root-systemic action
*Myzus persicae*

| Active compounds | Concentration of active compound in ppm | Kill rate in % after $10^d$ (days) |
|---|---|---|
| I-1 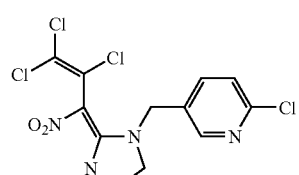 according to the invention | 20 | 100 |
| I-2 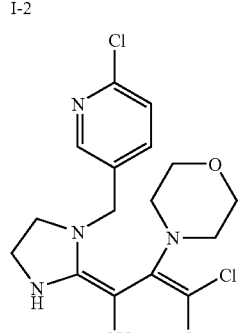 according to the invention | 20 | 100 |

Example G

*Myzus* Test

| Solvent: | 7 parts by weight of dimethylformamide |
|---|---|
| Emulsifier: | 2 parts by weight of alkylaryl polyglycol ether |

To produce a suitable preparation of active compound, 1 part by weight of active compound is mixed with the stated amounts of solvent and emulsifier, and the concentrate is diluted with emulsifier-containing water to the desired concentration.

Cabbage leaves (*Brassica oleracea*), which are heavily infested by the green peach aphid (*Myzus persicae*) are treated by being dipped into the preparation of active compound of the desired concentration.

After the desired period of time, the kill in % is determined. 100% means that all aphids have been killed; 0% means that none of the aphids have been killed.

In this test, for example, the following compounds of the Preparation Examples show good activity:

TABLE G

Plant-damaging insects
*Myzus* test

| Active compounds | Concentration of active compound in ppm | Kill rate in % after $6^d$ (days) |
|---|---|---|
| I-2 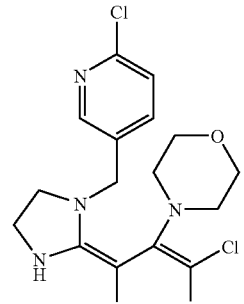 according to the invention | 500 | 100 |
| I-11 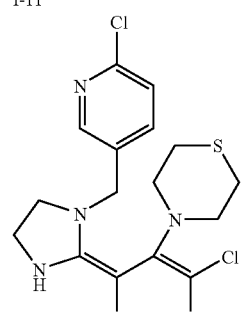 according to the invention | 500 | 100 |

Example H

*Phaedon* Larvae Test

| Solvent: | 7 parts by weight of dimethylformamide |
|---|---|
| Emulsifier: | 2 parts by weight of alkylaryl polyglycol ether |

To produce a suitable preparation of active compound, 1 part by weight of active compound is mixed with the stated amounts of solvent and emulsifier, and the concentrate is diluted with emulsifier-containing water to the desired concentration.

Cabbage leaves (*Brassica oleracea*) are treated by being dipped into the preparation of active compound of the desired concentration and are populated with larvae of the mustard beetle (*Phaedon cochleariae*) while the leaves are still moist.

After the desired period of time, the kill in % is determined. 100% means that all beetle larvae have been killed; 0% means that none of the beetle larvae have been killed.

In this test, for example, the activity of the following compounds of the Preparation Examples is superior to that of compounds of the prior art:

TABLE H

Plant-damaging insects
*Phaedon* larvae test

| Active compounds | Concentration of active compound in ppm | Kill rate in % after 6$^d$ (days) |
| --- | --- | --- |
| I-2 | 500 | 100 |

[Structure: 6-chloropyridin-3-ylmethyl imidazolidine with morpholine and dichloro-nitro vinyl group]

according to the invention

| I-11 | 500 | 100 |

[Structure: 6-chloropyridin-3-ylmethyl imidazolidine with thiomorpholine and dichloro-nitro vinyl group]

according to the invention

Example I

*Bemisia* Test

| Solvent: | 7 parts by weight of dimethylformamide |
| --- | --- |
| Emulsifier: | 2 parts by weight of alkylaryl polyglycol ether |

To produce a suitable preparation of active compound, 1 part by weight of active compound is mixed with the stated amounts of solvent and emulsifier, and the concentrate is diluted with water to the desired concentrations.

Cotton plants (*Gossypium hirsutum*) infected by eggs, larvae and pupae of the white fly (*Bemisia tabaci*) are dipped into a preparation of active compound of the desired concentration.

After the desired period of time, the kill in % is determined. 100% means that all animals have been killed; 0% means that none of the animals have been killed.

TABLE I

Plant-damaging insects
*Bemisia* test

| Active compounds | Concentration of active compound in ppm | Kill rate in % after 6$^d$ (days) |
| --- | --- | --- |
| I-2 | 500 | 100 |

[Structure: 6-chloropyridin-3-ylmethyl imidazolidine with morpholine and dichloro-nitro vinyl group]

according to the invention

| I-10 | 500 | 100 |

[Structure: 6-chloropyridin-3-ylmethyl imidazolidine with pyrrolidine and dichloro-nitro vinyl group]

according to the invention

Example J

*Spodoptera frugiperda* Test

| Solvent: | 7 parts by weight of dimethylformamide |
| --- | --- |
| Emulsifier: | 2 parts by weight of alkylaryl polyglycol ether |

To produce a suitable preparation of active compound, 1 part by weight of active compound is mixed with the stated amounts of solvent and emulsifier, and the concentrate is diluted with emulsifier-containing water to the desired concentration.

Cabbage leaves (*Brassica oleracea*) are treated by being dipped into the preparation of active compound of the desired concentration and are populated with caterpillars of the armyworm (*Spodoptera frugiperda*) while the leaves are still moist.

After the desired period of time, the kill in % is determined. 100% means that all caterpillars have been killed; 0% means that none of the caterpillars have been killed.

In this test, for example, the following compounds of the Preparation Examples show good activity:

TABLE J

Plant-damaging insects

*Spodoptera frugiperda* test

| Active compounds | Concentration of active compound in ppm | Rate of activity after 7$^d$ (days) |
|---|---|---|
| I-12 | 500 | 100 |

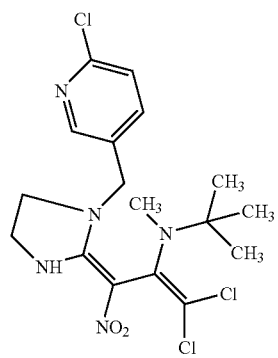

according to the invention

Example K

Critical Concentration Test/Root-Systemic Action

| Test insect: | *Myzus persicae* |
|---|---|
| Solvent: | 4 parts by weight of acetone |
| Emulsifier: | 1 part by weight of alkylaryl polyglycol ether |

To produce a suitable preparation of active compound, 1 part by weight of active compound is mixed with the stated amount of solvent, the stated amount of emulsifier is added and the concentrate is diluted with water to the desired concentration.

The preparation of active compound is mixed intimately with the soil. Here, the concentration of the active compound in the preparation is virtually immaterial, only the amount by weight of active compound per volume unit of soil, which is stated in ppm (mg/ml) matters. The treated soil is filled into pots of a volume of 250 ml, and pregerminated broad beans are planted into these pots. In this way, the active compound can be taken up from the soil by the plant roots and be transported into the leaves.

To demonstrate the root-systemic effect, after 7 days, the plants are populated with the test animals mentioned above and, after a further 7 days, evaluation is carried out by counting or estimating the number of dead animals. The root-systemic action of the active compound is derived from the kill rate. It is 100% if all test animals have been killed and 0% if the number of test insects still alive is exactly the same as in the untreated control.

Active compounds, application rates and results are shown in the table below:

TABLE K

Soil insects
Critical concentration/root-systemic test

| Active compounds | Concentration of active compound in 4 ppm % kill after weeks | | | |
|---|---|---|---|---|
| I-1 | 2 | 3 | 4 | 5 |
| | 100 | 100 | 99 | 100 |

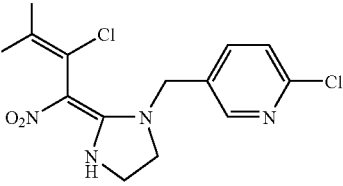

according to the invention

| I-2 | 2 | 3 | 4 |
| | 100 | 100 | 99 |

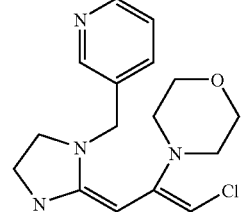

according to the invention

Example L

Test with Cat Fleas/Oral Uptake

| Test animals: | Adults of *Ctenocephalides felis* |
|---|---|
| Solvent: | Dimethyl sulphoxide (DMSO) |

To produce a suitable formulation, a suitable solution of active compound is prepared from 20 mg of active compound and 1 ml of DMSO. 15 µl of this formulation are added to 3 ml of citrated cattle blood and stirred.

10 unfed adult fleas (*Ctenocephalides felis*, strain "Georgi") are placed into a chamber (Ø 3.2 cm) whose top and bottom are closed with gauze. A metal cylinder whose underside is covered with parafilm is placed onto the chamber. The cylinder contains the 3 ml of blood/active compound formulation which can be taken up by the fleas through the paraffin membrane. Whereas the blood is warmed to 37° C., the temperature in the area of the flea chambers is adjusted to 25° C. Controls are mixed with the same volume of DMSO, without addition of a compound. The determinations are carried out in triplicate.

After 28 h, the mortality in % (=dead fleas) is determined.

Compounds which effect at least 25% kill of the fleas within 28 h are judged to be effective.

TABLE L

*Ctenocephalides felis*, orally

| Compound | Concentration in ppm | % action/kill |
|---|---|---|
| I-4 | 100 | 40 |
| I-3 | 100/20 | 50/0 |
| I-2 | 100/20/4/0.8 | 80/80/0/0 |
| I-10 | 100/20 | 100/40 |
| I-9 | 100/20 | 80/30 |
| I-12 | 100/20 | 70/30 |
| I-11 | 100/20 | 70/0 |
| I-13 | 100/20 | 100/20 |

Example M

Test with Flies (*Musca domestica*)

| Test animals: | adult *Musca domestica*, Reichswald strain (OP, SP, carbamate-resistant) |
|---|---|
| Solvent: | Dimethyl sulphoxide |

20 mg of active compound are dissolved in 1 ml of dimethyl sulphoxide, more dilute concentrations are prepared by dilution with dist. H$_2$O.

2 ml of this active compound preparation are pipetted onto filter paper discs (Ø 9.5 cm) in Petri dishes of corresponding dimensions. After the filter discs have been dried, 25 test animals are transferred into the Petri dishes, which are then covered.

After 1, 3, 5, 24 and 48 hours, the activity of the active compound preparation is determined. 100% means that all flies have been killed; 0% means that none of the flies have been killed.

In this test, for example, the activity of the following compounds of the Preparation Examples is superior to that of the compounds of the prior art:

TABLE M

*Musca domestica*

| Compound | Concentration in ppm | % action/kill |
|---|---|---|
| I-4 | 100/20 | 100/0 |
| I-2 | 100/20 | 50/0 |

Example N

Blowfly Larvae Test/Development-Inhibitory Action

| Test animals: | *Lucilia cuprina* larvae |
|---|---|
| Solvent: | Dimethyl sulphoxide |

20 mg of active compound are dissolved in 1 ml of dimethyl sulphoxide, more dilute concentrations are prepared by dilution with dist. H$_2$O.

About 20 *Lucilia cuprina* larvae are introduced into a test tube which contains about 1 cm$^3$ of horse meat and 0.5 ml of the preparation of active compound to be tested. After 24 and 48 hours, the efficacy of the preparation of active compound is determined. The test tubes are transferred into a beaker whose bottom is covered with sand. After a further 2 days, the test tubes are removed and the pupae are counted.

The efficacy of the preparation of active compound is assessed by the number of flies that have hatched after 1.5 times the period of development of an untreated control. 100% means that no flies have hatched; 0% means that all flies have hatched normally.

In this test, for example, the activity of the following compounds of the Preparation Examples is superior to that of the compounds of the prior art:

TABLE N

*Lucilia cuprina* (48 h)

| Compound | Concentration in ppm | % action/kill |
|---|---|---|
| I-1 | 100/20 | 100/0 |
| I-2 | 100/20 | 100/0 |
| I-12 | 100/20 | 100/0 |
| I-11 | 100/20 | 100/0 |
| I-13 | 100/20 | 100/0 |

What is claimed is:

1. A compound of formula (I)

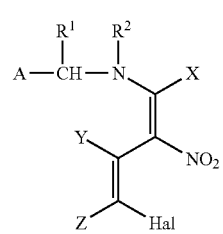

in which
A represents optionally substituted six-membered heterocyclyl or hetaryl containing a ring nitrogen atom,
R$^1$ represents hydrogen or alkyl,
R$^2$ represents hydrogen or alkyl,
Z represents halogen or NO$_2$,
Hal represents halogen,
X represents OR$^3$, SR$^3$, or NR$^4$R$^5$,
Y represents hydrogen, halogen, OR$^6$, SR$^6$, or NR$^7$R$^8$,
R$^3$ represents optionally substituted alkyl, alkenyl, cycloalkyl, or cycloalkylalkyl; or represents optionally substituted aryl or arylalkyl,
R$^4$ and R$^5$ independently of one another represent hydrogen; represent optionally substituted alkyl, alkenyl, alkynyl, cycloalkyl, cycloalkylalkyl, or alkoxycarbonyl; or represent optionally substituted aryl or arylalkyl; or R$^4$ and R$^5$ together with the nitrogen atom to which they are attached represent an optionally substituted ring,
R$^6$ represents optionally substituted alkyl, alkenyl, cycloalkyl, or cycloalkylalkyl; or represents optionally substituted aryl or arylalkyl, and
R$^7$ and R$^8$ independently of one another represent optionally substituted alkyl, alkenyl, cycloalkyl, or cycloalkylalkyl; or represent optionally substituted aryl or arylalkyl, or R$^7$ and R$^8$ together with the nitrogen atom to which they are attached represent an optionally substituted ring that is optionally interrupted by one or more heteroatoms selected from the group consisting of nitrogen, oxygen, and sulphur, or $R^2$ and $R^3$ together with the atoms linking them form an optionally substituted ring.

2. A compound of formula (I) according to claim 1 in which

A represents optionally substituted six-membered heterocyclyl containing a ring nitrogen atom or optionally substituted hetaryl wherein the hetaryl group is selected from the group consisting of pyridyl, pyrazinyl, and pyrimidinyl, $R^1$ represents hydrogen or straight-chain or branched alkyl having 1 to 6 carbon atoms, $R^2$ represents hydrogen or straight-chain or branched alkyl having 1 to 6 carbon atoms, Z represents halogen or $NO_2$, Hal represents halogen, X represents $OR^3$, $SR^3$, or $NR^4R^5$, Y represents hydrogen, halogen, $OR^6$, $SR^6$, or $NR^7R^8$, $R^3$ represents optionally substituted straight-chain or branched alkyl having 1 to 6 carbon atoms, optionally substituted straight-chain or branched alkenyl having 2 to 6 carbon atoms, optionally substituted mono-, bi-, or tricyclic cycloalkyl having 3 to 10 carbon atoms, or optionally substituted mono-, bi-, or tricyclic cycloalkylalkyl; or represents optionally substituted aryl wherein the aryl group is selected from the group consisting of phenyl, naphthyl, tetrahydronaphthyl, indanyl, and fluorenyl, or optionally substituted arylalkyl having 6 or 10 carbon atoms in the aryl moiety and 1 to 4 carbon atoms in the alkyl moiety in which the alkyl moiety is straight-chain or branched, $R^4$ and $R^5$ independently of one another represent hydrogen; represent optionally substituted straight-chain or branched alkyl having 1 to 6 carbon atoms, straight-chain or branched alkenyl having 2 to 6 carbon atoms, straight-chain or branched alkynyl having 2 to 6 carbon atoms, mono-, bi-, or tricyclic cycloalkyl having 3 to 10 carbon atoms, mono-, bi-, or tricyclic cycloalkylalkyl, or straight-chain or branched alkoxycarbonyl having I to 6 carbon atoms in the alkoxy moiety; or represent optionally substituted aryl wherein the aryl group is selected from the group consisting of phenyl, naphthyl, tetrahydronaphthyl, indanyl, and fluorenyl, or optionally substituted arylalkyl having 6 or 10 carbon atoms in the aryl moiety and 1 to 4 carbon atoms in the alkyl moiety in which the alkyl moiety is straight-chain or branched; or $R^4$ and $R^5$ together with the nitrogen atom to which they are attached represent an optionally substituted ring, $R^6$ represents optionally substituted straight-chain or branched alkyl having 1 to 6 carbon atoms, optionally substituted straight-chain or branched alkenyl having 2 to 6 carbon atoms, optionally substituted mono-, bi-, or tricyclic cycloalkyl having 3 to 10 carbon atoms, or optionally substituted mono-, bi-, or tricyclic cycloalkylalkyl; or represents optionally substituted aryl wherein the aryl group is selected from the group consisting of phenyl, naphthyl, tetrahydronaphthyl, indanyl, and fluorenyl, or optionally substituted arylalkyl having 6 or 10 carbon atoms in the aryl moiety and 1 to 4 carbon atoms in the alkyl moiety in which the alkyl moiety is straight-chain or branched, and $R^7$ and $R^8$ independently of one another represent optionally substituted straight-chain or branched alkyl having 1 to 6 carbon atoms, optionally substituted straight-chain or branched alkenyl having 2 to 6 carbon atoms, optionally substituted mono-, bi-, or tricyclic cycloalkyl having 3 to 10 carbon atoms, or optionally substituted mono-, bi-, or tricyclic cycloalkylalkyl; or represent optionally substituted aryl wherein the aryl group is selected from the group consisting of phenyl, naphthyl, tetrahydronaphthyl, indanyl, and fluorenyl, or optionally substituted arylalkyl having 6 or 10 carbon atoms in the aryl moiety and 1 to 4 carbon atoms in the alkyl moiety in which the alkyl moiety is straight-chain or branched; or R7 and R8 together with the nitrogen atom to which they are attached represent an optionally substituted ring that is optionally interrupted by one nitrogen, oxygen, or sulphur atom, or $R^2$ and $R^3$ together with the atoms linking them form an optionally $C_1$-$C_4$-alkyl-substituted $C_2$-$C_4$-alkylidene-diyl group.

3. A composition for controlling animal pests comprising one or more compounds of formula (I) according to claim 1 and one or more extenders and/or surfactants.

4. A process for preparing pesticides comprising mixing one or more compounds of formula (I) according to claim 1 with one or more extenders and/or surfactants.

5. A compound of formula (I) according to claim 1 in which

A represents optionally substituted pyridyl, $R^1$ represents hydrogen or straight-chain or branched alkyl having 1 to 6 carbon atoms, $R^2$ represents hydrogen or straight-chain or branched alkyl having 1 to 6 carbon atoms, Z represents halogen or $NO_2$, Hal represents halogen, X represents $OR^3$, $SR^3$, or $NR^4R^5$, Y represents hydrogen, halogen, $OR^6$, $SR^6$, or $NR^7R^8$, R3 represents optionally substituted straight-chain or branched alkyl having 1 to 6 carbon atoms, optionally substituted straight-chain or branched alkenyl having 2 to 6 carbon atoms, optionally substituted mono-, bi-, or tricyclic cycloalkyl having 3 to 10 carbon atoms, or optionally substituted mono-, bi-, or tricyclic cycloalkylalkyl; or represents optionally substituted aryl wherein the aryl group is selected from the group consisting of phenyl, naphthyl, tetrahydronaphthyl, indanyl, and fluorenyl, or optionally substituted arylalkyl having 6 or 10 carbon atoms in the aryl moiety and 1 to 4 carbon atoms in the alkyl moiety in which the alkyl moiety is straight-chain or branched, $R^4$ and $R^5$ independently of one another represent hydrogen; represent optionally substituted straight-chain or branched alkyl having 1 to 6 carbon atoms, straight-chain or branched alkenyl having 2 to 6 carbon atoms, straight-chain or branched alkynyl having 2 to 6 carbon atoms, mono-, bi-, or tricyclic cyclo-alkyl having 3 to 10 carbon atoms, mono-, bi-, or tricyclic cycloalkylalkyl, or straight-chain or branched alkoxycarbonyl having 1 to 6 carbon atoms in the alkoxy moiety; or represent optionally substituted aryl wherein the aryl group is selected from the group consisting of phenyl, naphthyl, tetrahydronaphthyl, indanyl, and fluorenyl or optionally substituted arylalkyl having 6 or 10 carbon atoms in the aryl moiety and 1 to 4 carbon atoms in the alkyl moiety in which the alkyl moiety is straight-chain or branched; or $R^4$ and $R^5$ together with the nitrogen atom to which they are attached represent an optionally substituted ring, $R^6$ represents optionally substituted straight-chain or branched alkyl having 1 to 6 carbon atoms, optionally substituted straight-chain or branched alkenyl having 2 to 6 carbon atoms, optionally substituted mono-, bi-, or tricyclic cycloalkyl having 3 to 10 carbon atoms, or optionally substituted mono-, bi-, or tricyclic cycloalkylalkyl; or represents optionally substituted aryl wherein the aryl group is selected from the group consisting of phenyl, naphthyl, tetrahydronaphthyl, indanyl, and fluorenyl, or optionally substituted arylalkyl having 6 or 10 carbon atoms in the aryl moiety and 1 to 4 carbon atoms in the alkyl moiety in which the alkyl moiety is straight-chain or branched, and $R^7$ and $R^8$ independently of one another represent optionally substituted straight-chain or branched alkyl having 1 to 6 carbon atoms, optionally substituted straight-chain or branched alkenyl having 2 to 6 carbon atoms, optionally substituted mono-, bi-, or tricyclic cycloalkyl having 3 to 10 carbon atoms, or optionally substituted mono-, bi-, or tricyclic cycloalkylalkyl, or $R^7$ and $R^8$ together with the nitrogen atom to which they are attached represent an optionally substituted ring that is optionally interrupted by one nitrogen, oxygen, or sulphur atom, or $R^2$ and $R^3$ together with the atoms linking them form an optionally $C_1$-$C_4$-alkyl-substituted $C_2$-$C_4$-alkylidene-diyl group.

* * * * *